(12) United States Patent
Kang et al.

(10) Patent No.: US 9,518,126 B2
(45) Date of Patent: Dec. 13, 2016

(54) VACCINE COMPRISING MONOCYTE OR IMMATURE MYELOID CELLS (IMC) WHICH WERE LOADED WITH THE LIGAND OF NATURAL KILLER T CELL AND ANTIGEN

(75) Inventors: Chang-Yuil Kang, Seoul (KR); Hyun-Jeong Ko, Seoul (KR); Jung-Mi Lee, Seoul (KR); Yeon-Jeong Kim, Changwon-si (KR)

(73) Assignee: CELLID CO., LTD., Seoul (KR)

( * ) Notice: Subject to any disclaimer, the term of this patent is extended or adjusted under 35 U.S.C. 154(b) by 760 days.

(21) Appl. No.: 12/279,166

(22) PCT Filed: Nov. 28, 2007

(86) PCT No.: PCT/KR2007/006057
§ 371 (c)(1),
(2), (4) Date: Aug. 12, 2008

(87) PCT Pub. No.: WO2009/066824
PCT Pub. Date: May 28, 2009

(65) Prior Publication Data
US 2009/0285851 A1    Nov. 19, 2009

(30) Foreign Application Priority Data

Nov. 19, 2007   (KR) .................. 10-2007-0118066

(51) Int. Cl.
A61K 31/164    (2006.01)
C12N 5/0786    (2010.01)
A61K 39/00     (2006.01)
C07K 16/32     (2006.01)

(52) U.S. Cl.
CPC ............ *C07K 16/32* (2013.01); *A61K 31/164* (2013.01); *A61K 39/00* (2013.01); *C12N 5/0645* (2013.01); *A61K 2039/5154* (2013.01); *A61K 2039/5158* (2013.01); *C12N 2501/999* (2013.01)

(58) Field of Classification Search
CPC ............ C12N 5/0645; C12N 2502/1157; C12N 2506/115; A61K 35/15; A61K 2039/5154; A61K 2039/5158; A61K 39/00
See application file for complete search history.

(56) References Cited

U.S. PATENT DOCUMENTS

2002/0177551 A1* 11/2002 Terman .................... 514/12
2006/0142546 A1* 6/2006 Hanisch .............. C07K 14/4727
                                                    530/322
2010/0233215 A1* 9/2010 Fujii .................. A61K 39/0011
                                                    424/277.1
2012/0082688 A1* 4/2012 Chen .................... A01N 1/0284
                                                    424/184.1

FOREIGN PATENT DOCUMENTS

WO   WO/2007/097370 A1 * 8/2007 ............ C12N 15/00

OTHER PUBLICATIONS

Byers, T. (CA Cancer Journal, vol. 49, No. 6, Nov./Dec. 1999).*
Marincola et al. (Trends in Immunology, Jun. 2003, 24: 334-341).*
Harlin et al. (Caner Immunol. Immunotherap. 2006, 55: 1185-1197).*
Kirkin et al. (1998, APMIS, 106: 665-679).*
Sherman et al. (Critical Reviews in Immunol. 1998, 18:47-54).*
Wheeler (Salud Publica Mex, (Jul.-Aug. 1997) 39 (4) 283-7).*
Efferson et al. (Anticancer research, 2005, vol. 25, pp. 715-24).*
Bachman et al. (Journal of Immunology, 2005, vol. 175, pp. 4677-4685).*
Ko et al. (Cancer Res. Aug. 1, 2007 67: 7477-7486).*
Wu et al. (J. Immunology, 2006 177: 934-943).*
Chung et al. (Blood, Jul. 2005 106: 201-206).*
Franklin et al. (Cancer Cell Apr. 2004 5: 317-328).*
Kawamoto and Minato (IJBCB 2004 36: 1374-1379).*
Ziegler-Heitbrock, L. ( J. Leukocyte Biol. Mar. 2007, 81: 584-592).*
MUC1 protein, human, (NCBI MeSH http://www.ncbi.nlm.nih.gov/mesh/67060192, Aug. 9, 1989).*
Joosten et al. (Arthritis Res. Oct. 26, 1999; 1(1): 81-91).*
Angulo et al. (Blood Jan. 1, 2000 95(1): 212-220).*
Goñi et al. (Internat. Immunology 2002 14 (10): 125-1134).*
Idiotype (Medical dictionary http://medical-dictionary.thefreedictionary.com/idiotype, May 19, 2016).*
Moodycliffe et al., "Immune suppression and skin cancer development: regulation by NKT cells," *Nature Immunology* (2000) 1 (6): 521-525.
Kawano et al., "CD1d-restricted and TCR-mediated activation of Vα14 NKT cells by glycosylceramides," *Science* (1997) 278: 1626-1629.
Chang et al., "Potent immune-modulating and anticancer effects of NKT cell stimulatory glycolipids." *PNAS* 104:25(2007): 10299-10304.

(Continued)

*Primary Examiner* — Peter J Reddig
(74) *Attorney, Agent, or Firm* — Lucas & Mercanti, LLP

(57) ABSTRACT

The present invention relates to an immuno-therapeutic and prophylactic vaccine comprising monocytes or immature myeloid cells (IMCs) loaded with the ligand of natural killer T cell and an antigen for the prevention and treatment of infectious disease or cancer, more precisely, an immuno-therapeutic and prophylactic vaccine comprising monocytes or IMCs loaded with α-galactosylceramide (αGalCer), a kind of glycolipid and a natural killer T cell ligand, and antigen. Monocytes or immature myeloid cells (IMCs) therein, which are easily obtainable, unlike dendritic cells, not only induce a significant level of cytotoxic T lymphocyte responses but also have a prophylactic and therapeutic effect on malignant tumor. Therefore, the immuno-therapeutic and prophylactic vaccine of the present invention can be effectively used as an immunotherapeutic agent.

7 Claims, 13 Drawing Sheets

(56) References Cited

OTHER PUBLICATIONS

Chung et al., "CD1d-Restricted T cells license B cells to generate long-lasting cytotoxic antitumor immunity In vivo." *Cancer Res.* 66:13(2006): 6843-6850.

Giaccone et al., "A Phase I study of the natural killer T-cell Ligand α-Galactosylceramide (KRN7000) in patients with solid tumors." *Clinical Cancer Research* 8(2002): 3702-3709.

Kronenberg, Mitchell. "Toward an understanding of NKT cell biology: Progress and paradoxes." *Annu. Rev. Immunol.* 26(2005): 877-900.

Nieda et al., "Theraputic activation of Vα24+Vβ11+NKT cells in human subjects results in highly coordinated secondary activation aof acquired an innate immunity." *Blood* 103:2(2004): 383-389.

Chen et al., "Cultured NK1.1+CD4+ T cells produce large amounts of IL-4 and IFN-γ upon activation by anti-CD3 or CD1," *J. Immunol.* (1997) 159: 2240-2249.

Wilson et al., "The response of natural killer T cells to glycolipid antigens is characterized by surface receptor down-modulation and expansion," *PNAS* (2003) 100: 10913-10918.

van der Vilet et al., "Potent expansion of human natural killer T cells using α-galactosylceramide (KRN7000)-loaded monocyte-derived dendritic cells, cultured in the presence of IL-7 and IL-15," *Journal of Immunological Methods* (2001) 247: 61-72.

Penichet et al., "In vivo properties of three human HER2/neu-expressing murine cell lines in immunocompetent mice," *Laboratory Animal Science* (1999) 49 (2): 179-188.

Mattner et al., "Exogenou and endogenous glycolipid antigens activate NKT cells during microbial infections," *Letters to Nateure* (2005) 434: 525-50.

Kinjo et al., "Recognition of bacterial glycosphingolipids by natural killer T cells," *Nature* (2005) 434: 520-525.

Sriram et al., "Cell wall glycosphingolipids of *Sphingomonas paucimobilis* are CD1d-specific ligands for NKT cells," *Eur. J. Immunol.*(2005) 35: 1692-1701.

Fischer et al., "Mycobacterial phosphatidylinositol mannoside is a natural antigen for CD1d-restricted T cells," *PNAS* (2004) 101 (29): 10685-10690.

Zhou et al., "Lysosomal glycosphingolipid recognition by NKT cells," *Science* (2004) 306: 1786-1789.

Wu et al., "Cross-presentation of disialoganglioside GD3 to natural killer T cells," *J. Exp. Med.* (2003) 198: 173-181.

Giabbai et al., "Crystal structure of mouse CD1d bound to the self ligand phosphatidylcholine: A molecular basis for NKT cell activation," *The Journal of Immunology* (2005) 175: 977-984.

Gumperz et al., "Murine CD1d-restricted T cell recognition of cellular lipids," *Immunity* (2000) 12: 211-221.

Jahng et al., "Prevention of autoimmunity by targeting a distinct, noninvariant CD1d-reactive T cell population reactive to sulfatide," *J. Exp. Med.* (2004) 199: 947-957.

Ortaldo et al., "Dissociation of NKT stimulation, cytokine induction, and NK activation in vivo by the use of distinct TCR-binding ceramides," *The Journal of Immunology* (2004): 943-953.

Amprey et al., "A subset of liver NKT cells is activated during *Leishmania donovani* infection by CD1d-bound lipophosphoglycan," *The Journal of Experimental Medicine* (2004) 200:895-904.

Parekh et al., "Quantitative and qualitative differences in the In Vivo response of NKT cells to distinct α- and β-Anomeric glycolipids," *The Journal of Immunology* (2004): 3694-3706.

Miyamoto et al., "A synthetic glycolipid prevents autoimmune encephalomyelitis by inducing TH2 bias of natural killer T cells," *Nature* (2001) 413: 531-534.

Yang et al., "The C-glycoside analogue of the immunostimulant α-galactosylceramide (KRN7000): Synthesis and striking enhancement of activity," *Agnew. Chem. Int. Ed.* (2004): 43:3818-3822.

Goff et al., "Effects of lipid chain lengths in α-galactosylceramides on cytokine release by natural killer T cells," *J. Am. Chem. Soc.* (2004) 126 (42): 13602-13603.

Wu et al., "Bacterial glycolipids and analogs as antigens for CD1d-restricted NKT cells," *PNAS* (2005) 102 (5): 1351-1356..

Fujio et al, "Structure-based discovery of glycolipids for CD1d-mediated NKT cell activation: Tuning the adjuvant versus immunosuppression activity," *J. Am. Chem. Soc.* (2006) 128 (28): 9022-9023.

Liu et al., "A modified α-galactosyl ceramide for staining and stimulating natural killer T cells," *Journal of Immunological Methods* (2006) 312: 34-39..

Lee et al., "Synthesis and evaluation of 1,2,3-Triazole containing analogues of the immunostimulant α-GalCer," *Journal of Medicinal Chemistry* (2007) 50 (3): 585-589.

Chang et al., "Potent immune-modulating and anticancer effects of NKT cell stimulatory glycolipids," *PNAS* (2007) 104 (25): 10299-10304.

Moody et al., "CD1b-mediated T cell recognition of a glycolipid antigen generated from mycobacterial lipid and host carbohydrate during infection," *J. Exp. Med.* (2000) 192 (7): 965-976.

Nakagawa et al., "Treatment of hepatic metastasis of the colon26 adenocarcinoma with an α-galactosylceramide, KRN7000," *Cancer Research* (1998) 58: 1202-1207.

Giaccone et al., "A phase 1 study of the natural killer T-cell ligand α-galactosylceramide (KRN7000) in patients with solid tumors," *Clinical Cancer Research* (2002) 8: 3702-3709.

Spada et al., "Low expression level but potent antigen presenting function of CD1d on monocyte lineage cells," *Eur. J. Immunol.* (2000) 30: 3468-3477.

Chang et al., "Sustained expansion of NKT cells and antigen-specific T cells after injection of α-galactosyl-cermide loaded mature dendritic cells in cancer patients," *The Journal of Experimental Medicine* (2005) 9: 1503-1517.

Takahashi et al, "Cuttingi edge: Analysis of human Vα24+CD8+ NK T cells activated by α-galactosylceramide-pulsed monocyte-derived dendritic cells," *J. Immunol.* (2002) 168: 3140-3144.

Park et al., "CD1-restricted T-cell responses and microbial infection," *Nature* (2000) 406: 788-792.

Yu et al., "Modulation of CDld-restricted NKT cell responses by using N-acyl variants of α-galactosylceramides," *PNAS* (2005) 102 (9): 3383-3388.

Wilson et al., Most Lymphoid Organ Dendritic Cell Types Are Phenotypically and Functionally Immature, Blood, Sep. 15, 2003, p. 2187-2194, vol. 102, No. 6.

\* cited by examiner

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: H-2Kb-presented ovalbumin 257-264 aa peptide

<400> SEQUENCE: 1

Ser Ile Ile Asn Phe Glu Lys Leu
1               5
```

VACCINE COMPRISING MONOCYTE OR IMMATURE MYELOID CELLS (IMC) WHICH WERE LOADED WITH THE LIGAND OF NATURAL KILLER T CELL AND ANTIGEN

This application is a National Stage Application of PCT/KR2007/006057, filed Nov. 28, 2007, which claims benefit of Serial No. 10-2007-0118066, filed Nov. 19, 2007 in South Korea and which application(s) are incorporated herein by reference. A claim of priority to all, to the extent appropriate is made.

TECHNICAL FIELD

The present invention relates to an immuno-therapeutic and prophylactic vaccine comprising monocytes or immature myeloid cells (IMCs) loaded with the ligand of natural killer T cell and antigen for the prevention and treatment of infectious disease or cancer, more precisely, an immuno-therapeutic and prophylactic vaccine comprising monocytes or IMCs loaded with α-galactosylceramide (αGalCer), a kind of glycolipid and a natural killer T cell ligand, and antigen.

BACKGROUND ART

Owing to the advancement of medical science, the survival rate of cancer patients is increasing. However, the rate of cancer development is also increasing according to the change of environmental factors and extended average life span. Up to date, many studies have been undergoing to treat cancer, and accordingly new drugs and treatment methods for cancer have been developed with improved treatment effect on cancer patients. However, in spite of the breakthrough in cancer treatment agents and methods such as surgery, radiotherapy and chemotherapy, the treatment effect on malignant tumor is still limited. Furthermore, side effects resulted from non-specific cytotocixity and relapse of cancer are still problems to be taken care of. To overcome the above problems, a new treatment method has been actively tried and under development, including immunotherapy. Immunotherapy has advantages of reducing side effects caused by systemic toxicity by inducing tumor-specific toxicity and improving the conventional cancer treatment method by establishing positive memory response against tumor antigen.

Anticancer cellular vaccine using antigen presenting cells can activate CD8+ T cells and CD4+ T cells effectively, resulting in excellent anticancer effect. The most frequently used cells for antigen presenting cell vaccine are dendritic cells, which uptake antigen and present thereof to effector cells along with costimulatory signal and therefore the dendritic cells can activate effector cells and induce strong immune responses. The cellular immunotherapeutic agent using dendritic cells is prepared and treated to a patient by the following steps; separating dendritic cells or monocytes, the precursors of the dendritic cells, from bone marrow or peripheral blood of a patient; proliferating and differentiating thereof; introducing an antigen; and administering the cells to the patient. The administered dendritic cells present specific antigen to T cells and thereby activate T cells to induce antigen-specific immune responses effectively. In spite of such advantages, the development of the cellular immunotherapeutic agent using dendritic cells is still limited because the number of dendritic cells which exist in peripheral blood and lymphoid tissues is small and isolation of the dendritic cells is difficult and ex-vivo culture might be required for several days when the cells are differentiated from monocytes. Therefore, it is required to develop an alternative improved cellular immunotherapeutic agent.

It is well understood that invariant natural killer T cells (iNKT cells) play a crucial role in a variety of immune responses and in immunopathology as a whole. Ligand-mediated activation of iNKT cells lead to the activation of T, B and NK cells as well as dendritic cells. Injection of alpha-galactosylceramide (αGalCer), an iNKT ligand, generates antitumor immunity via the activation of NK and T cells (Moodycliffe A M et al., *Nat Immunol* 1:521-525, 2000). The iNKT cells govern the response to self- and exogenous-antigens and determine whether autoimmune or immune response will be induced (Kronenberg M, *Annu Rev Immunol* 23:877-900, 2005; Park S H & Bendelac A, *Nature* 406:788-792, 2000).

Alpha-galactosylceramide (αGalCer) is a kind of glycolipid extracted from marine sponge, which is the ligand of natural killer T cell (NKT cell) having Vα14+ T cell receptor (TCR) and presented to NKT cells by CD1d molecule on antigen presenting cells (APC) (Kawano et al., *Science* 278:1626, 1997). The activation of the natural killer T cells by the natural killer T cell ligand leads to the mass-production of cytokine such as IFN-γ and IL-4, by which immune responses against either specific disease or infection can be controlled (Chen et al., *J Immunol* 159:2240, 1997; Wilson et al., *Proc Natl Acad Sci* USA 100:10913, 2003).

Unlike in healthy people, the number of immature myeloid cells (IMCs) increased in cancer patients which include immature macrophages, granulocytes, immature dendritic cells, monocytes and myeloid cells in early differential stage. Significantly increased level of IMCs was also detected in blood, bone marrow, spleen and tumor tissues of an animal model transplanted with tumor cells. Particularly in a mouse model, the expressions of CD11b and Gr-1 are observed on the surface of IMCs. The level of $CD11b^+/Gr-1^+$ cells in a healthy mouse blood and spleen is as low as up to 4%, which is because that $CD11b^+/Gr-1^+$ cells are the precursors of macrophages and dendritic cells, so that they can be differentiated into mature macrophages and dendritic cells if proper cytokine is provided. In cancer patients, however, $CD11b^+/Gr-1^+$ cells are not differentiated any more and accumulated because of tumor derived factors (IL-6, IL-10, VEGF, GM-CSF, etc). Since IMCs are accumulated at high level in blood of a cancer patient, it is easy to obtain a large amount of the cells. In addition, when monocytes are isolated to produce dendritic cell vaccine, it is difficult to gate out a large number of IMCs. IMCs, proliferated and accumulated in cancer patients and animals transplanted with tumor, are known to inhibit immune system. However, it is highly expected to improve immunogenicity by giving a proper stimulus.

Recently, it has been proved that the immunogenicity of dendritic cells has been enhanced by activating natural killer T cells (Kronenberg M et al., *Annu Rev Immunol* 23:877-900, 2005; Park S H et al., *Nature* 406:788-792, 2000). Based on that, the present inventors activated natural killer T cells by presenting natural killer T cell ligand to B cells for the first time, and further induced cytotoxic T cell responses against the antigen loaded on B cells by increasing immunogenicity of the B cells with the help of natural killer T cell, followed by confirmation that the effect was similar to that of dendritic cell vaccine (Chung Y et al., *Cancer Res* 66(13):6843-6850, 2006). However, there is no report saying that the improvement of immunogenicity by the activation of natural killer T cells might be exhibited not only in B cells but also in monocytes, the precursors of dendritic cells, or in immature myeloid cells (IMCs). Thus, in order to investigate whether monocytes and IMCs can be effectively used for the anticancer cellular vaccine, the present inventors loaded both antigen peptide and αGalCer to monocytes or IMCs, or loaded αGalCer to monocytes or IMCs which were transduced with adenovirus expressing an antigen, which was then administered into a subject. And further, the present inventors completed this invention by confirming thereby that immunization with monocytes- or IMCs-based vaccine induced the antigen specific immune responses and the significant anticancer effects.

DISCLOSURE

Technical Problem

It is an object of the present invention to provide an immunotherapeutic and prophylactic vaccine comprising monocytes or immature myeloid cells (IMCs) loaded with the ligand of natural killer T cell, particularly α-galactosylceramide (αGalCer), and an antigen, which can activate natural killer T cells and induces antigen-specific immune responses.

Technical Solution

To achieve the above object, the present invention provides an immunotherapeutic and prophylactic vaccine comprising monocytes or immature myeloid cells (IMCs) loaded with the ligand of natural killer T cell and an antigen.

The present invention also provides a natural killer T cell activator comprising monocytes or immature myeloid cells (IMCs) loaded with alpha-galactosylceramide (αGalCer).

The present invention further provides a cytotoxic response inducer comprising monocytes or immature myeloid cells (IMCs) expressing tumor antigen.

The present invention also provides a method for the immunotherapy and immune prevention for diseases comprising the step of administering the immunotherapeutic and prophylactic vaccine comprising monocytes or immature myeloid cells (IMCs) loaded with the ligand of natural killer T cell and the antigen to a subject.

Advantageous Effect

The composition of the present invention, monocytes or immature myeloid cells (IMCs), is easier to isolate than dendritic cells. Immunization with monocytes or immature myeloid cells (IMCs) loaded with the ligand of natural killer T cell, particularly αGalCer, and an antigen not only induces cytotoxic T cell responses at significant level but also induces preventive and therapeutic effects on malignant tumors. Therefore, the vaccine comprising the cells can be effectively used as a preventive and therapeutic agent for cancer. In addition, the vaccine of the present invention can induce immune responses even without the aid of CD4+ T cells. Therefore, it can be used to immunize a HIV infected patient who has immune deficiency caused by the lack of CD4+ T cells.

DESCRIPTION OF DRAWINGS

The application of the preferred embodiments of the present invention is best understood with reference to the accompanying drawings, wherein.

BEST MODE

Figure 1:
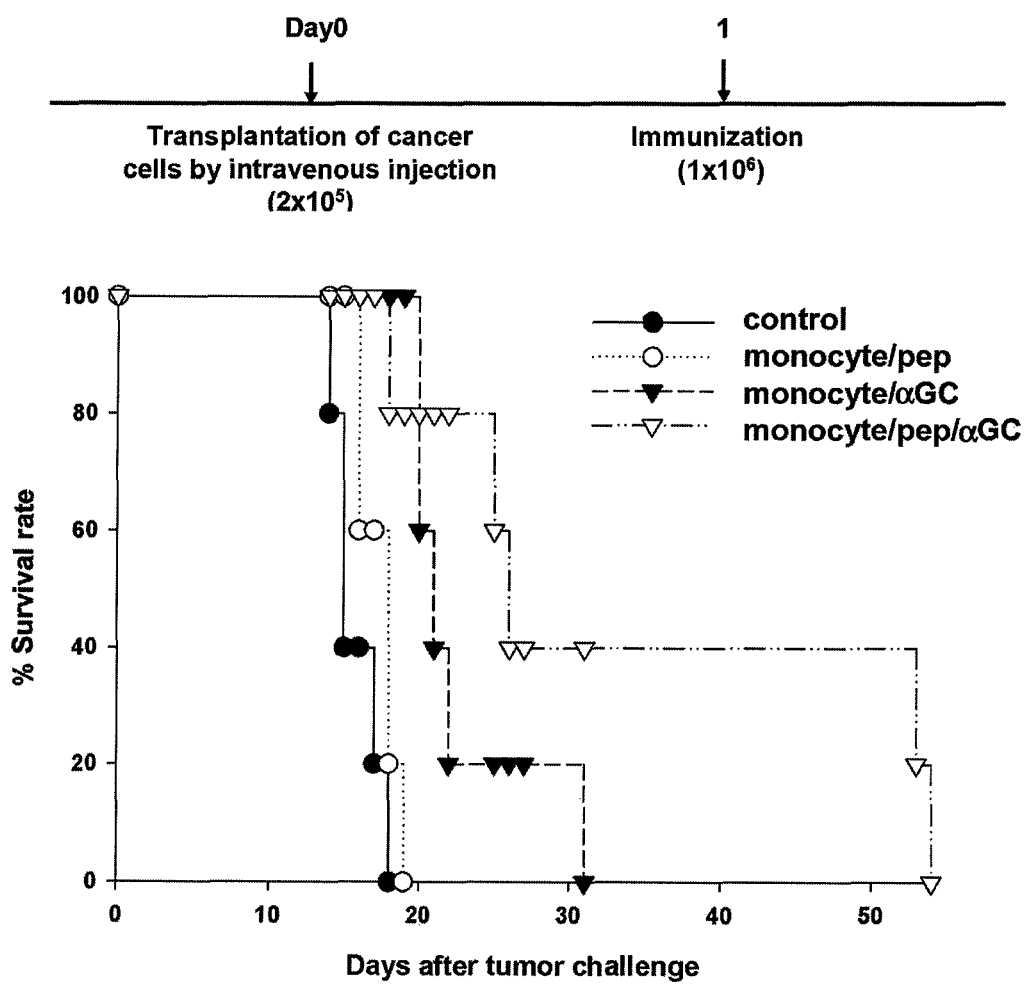
FIG. 1 is a diagram illustrating the anticancer effect of monocyte vaccine loaded with αGalCer and an antigen peptide.

Hereinafter, the present invention is described in detail.

Since it was already well established that alpha-galactosylceramide (αGalCer)-loaded dendritic cells (DCs) activate invariant Natural Killer T (iNKT) cells (van der Vliet H J et al., *J Immunol Methods* 1, 247(1-2):61-72, 2001), the present inventors examined whether☐αGalCer-loaded monocytes or IMCs would do likewise.

Monocytes are precursor cells originated from bone marrow and having potential for differentiation into dendritic cell (DC) or macrophages. The present inventors isolated monocytes expressing CD11b from a mouse and prepared monocyte vaccine loaded with αGalCer and an antigen peptide. The anticancer effect of the vaccine was investigated by using HER-2/CT26 (Penichet M L et al., *Lab Anim Sci* 49:179-88, 1999) cells expressing tumor associated antigen, Her-2/neu. As a result, the vaccine was confirmed to have significant anticancer effect (see FIG. 1). To confirm whether the vaccine could induce cytotoxic immune responses by activating antigen peptide-specific cytotoxic T lymphocytes, in vivo CTL assay was performed. As a result, cytotoxic immune response capable of destroying a target at high level was observed (see FIG. 6). In fact, only 1×10$^6$ cells were enough to induce effective cytotoxic immune response (see FIG. 7).

The cell vaccine loaded with an antigen peptide, however, is limited in clinical use to a haplotype of major histocompatibility complex (MHC). That is, the vaccine cannot be used generally and can present only single epitope. Unlike the above vaccine, the vaccine using a virus expressing an antigen is not limited to a haplotype of major histocompatibility complex and can be applied to every one since it delivers a whole antigen, and therefore this vaccine induces not only cell mediated immune responses but also humoral immune responses. Thus, the present inventors prepared monocyte vaccine loaded with αGalCer and transduced with adenovirus expressing an antigen and investigated its anticancer effect. As a result, the mouse transplanted with tumor and treated with the monocyte vaccine showed significant extension of survival period, suggesting that the vaccine has excellent anticancer effect on tumor cells (see FIG. 2). To investigate whether the vaccine could induce cytotoxic immune response by activating antigen peptide-specific cytotoxic T lymphocytes, in vivo CTL assay was performed. As a result, only 2×10$^6$ cells were enough to induce effective cytotoxic immune response (see FIG. 8). Compared with the monocyte vaccine loaded with an antigen peptide, this vaccine induced cytotoxic response at lower level, but this vaccine extended the survival period longer than the monocyte vaccine loaded with an antigen peptide. The above result suggests that the adenovirus vaccine induces additional immune responses in addition to cytotoxic T cell response. To confirm whether the monocyte vaccine transduced with adenovirus expressing an antigen could induce both cell mediated immune responses and humoral immunity, generation of Her-2/neu specific antibody by administration of the monocyte vaccine was investigated. As a result, the highest antibody generation was observed in the group administered with 2×10$^6$ cells, and the significant antibody generation was also observed in the group administered with 1×10$^6$ or 5×10$^5$ cells (see FIG. 12). However, the antibody generation was not detected in the group treated with less than 2.5×10$^5$ cells. In the meantime, IMC vaccine was prepared by the same manner as described above except the antigen peptide was replaced with ovalbumin. The vaccine was administered to C57BL/6 mice and cytotoxicity was investigated. As a result, effective cytotoxic response against ovalbumin antigen was confirmed, indicating that the immune responses induced by the IMC vaccine is not limited to a specific antigen but responding to various antigens (see FIG. 13).

In the mouse with transplantable tumors or chronic inflammation, the level of immature myeloid cells (IMCs) is significantly increased in the cancer and spleen, etc., and so is in peripheral blood of a cancer patient. The IMCs are the precursors of myeloid cells having potential for differentiation into various cells including granulocytes, monocytes, macrophages, and dendritic cells, and are known to accelerate tumor cell growth by suppressing the functions of cancer antigen specific or non-specific T lymphocytes by taking advantage of arginase I, nitrogen oxide, reactive oxygen species and TGF-β. It is also known that IMCs, which proliferate and accumulate in the tumor-bearing mouse, express Gr-1 and CD11b simultaneously on their surface and comprise monocytes-like cells with high portion. Thus, the present inventors investigated whether the IMCs-based cell vaccine prepared by the similar method with the one for monocyte vaccine had anticancer effect. The inventors isolated splenocytes from the mouse transplanted with Her-2/CT26 cells and then eliminated B cells and dendritic cells. αGalCer was loaded thereto and CD11b+ cells were separated, and then they were loaded with an antigen peptide to produce IMC vaccine. During the preparation of this vaccine, natural killer T cells and IMCs were coexisted, which means natural killer T cells recognize αGalCer loaded CD1d on IMCs and then activate IMCs, resulting in more effective IMC vaccine. The anticancer effect of the vaccine was investigated by using Her-2/CT26. As a result, the vaccine demonstrated significant anticancer effect (see FIG. 3). It was further investigated whether the vaccine induced cytotoxic immune response by activating peptide-specific cytotoxic T lymphocytes by in vivo CTL assay. As a result, a significant level of cytotoxic immune response was detected (see FIG. 9). The above results indicate that IMC vaccine has significant anticancer effect by inducing antigen specific cytotoxic immune response to destroy cancer cells.

The present inventors also prepared IMC vaccine loaded with αGalCer and transduced with adenovirus expressing an antigen, and investigated its anticancer effect. As a result, IMC vaccine administration extended survival period significantly, indicating excellent anticancer effect on tumor cells (see FIG. 4). The anticancer effect of the IMC vaccine was reduced significantly in the NK cells eliminated—(see FIG. 5a) or CD8+ cells eliminated—(see FIG. 5b) groups, suggesting that the two immune subsets play a key role in anticancer activity induced by IMC vaccination. On the other hand, the anticancer effect of the IMC vaccine was not reduced in the animal group where CD4+ cells were eliminated, compared with the normal group (see FIG. 5b), suggesting that the IMC vaccine can induce immune responses in the absence of CD4+ T cells. Therefore, the vaccine can be effectively treated to HIV patients for immunization whose CD4+ T cells are significantly reduced. It was further investigated whether the vaccine could induce cytotoxic immune response by activating peptide-specific cytotoxic T lymphocytes by in vivo CTL assay. As a result, the vaccine induced high level of cytotoxic immune response (see FIG. 10). This level was not so much high as the one induced by IMC vaccine loaded with a peptide. But, peptide-pulsed cellular vaccine was loaded only with single epitope peptide, whereas adenovirus-transduced cellular vaccine could present multiple epitope peptides. Besides, the transduction efficiency was not 100% and thus specific antigen peptide-specific cytotoxic immune response was estimated comparatively at low level. Nevertheless, this vaccine had an advantage of simultaneous induction of various immune responses. When immunization was induced by 8×10$^6$ cells of the vaccine, almost 90% cytotoxic immune response was induced, indicating that the IMC vaccine transduced with a virus induces cytotoxic immune responses effectively (see FIG. 11).

The present invention provides an immunotherapeutic and prophylactic vaccine comprising monocytes or immature myeloid cells (IMCs) loaded with the ligand of natural killer T cell and an antigen.

The ligand of natural killer T cell includes alpha-galacturonosylceramide (GSL-1') and alpha-glucuronosylceramide (GSL-1) (Mattner J et al., Nature 434:525, 2605; Kinjo Y et al., Nature 434:520, 2005), GSL-4 (Eur J Immunol 35:1692, 2005) originated from Sphingomonas spp., phosphatidylinositoltetramannoside originated from M. tuberculosis (Fischer K et al., PNAS 101:10685, 2004), autoantigens isoglobotrihexosylceramide (Zhou D et al., Science 306:1786, 2004) and ganglioside GD3 (Wu D Y et al., *J Exp Med* 198:173, 2003), phosphatidylcholine (*J Immunol* 175:977, 2005), phosphatidylethanolamine and phosphatidylinositol (*Immunity* 12:211), sulfatide (*J Exp Med* 199:947, 2004), beta-galactosylceramide (β-GalCer, Ortaldo J R et al., *J Immunol* 172:943), *Leishmania* surface glycosidic bond lipophosphoglycan and glycoinositol phospholipids (*J Exp Med* 200:895, 2004), αGalCer derivatives beta-anomeric GalCer and alpha-anomeric GalCer (*J Immunol* 173:3693, 2004), αGalCer variants (*Nature* 413:531, 2001; *Angew Chem Int Ed Engl* 43:3818, 2004; *J Am Chem Soc* 126:13602, 2004; *PNAS* 102:1351, 2004; *PNAS* 102:3383, 2005; *J Am Chem Soc* 128:9022, 2006; *J Immunol Methods* 312-34, 2006; *J Med Chem* 50:585, 2007; *PNAS* 104:10299, 2007) and bacteria lipid antigen such as glucose monomycolate originated from *Nocardia falcinica* (Moody D B et al., *J Exp Med* 192:965, 2000), but not always limited thereto.

The antigen herein can be any antigen capable of inducing immune responses as a vaccine, which is exemplified by an antigen derived from pathogen such as pathogenic bacteria, viruses and parasites, and a cancer antigen. At this time, a full length antigen or an antigen fragment can be used. The pathogenic bacteria derived antigen is exemplified by *Bordetella pertussis* antigen (pertussis toxin, filamentous haemagglutinin, pertactin), tetanus toxoid, diphtheria toxoid, *Helicobacterpylori* antigen (capsula polysaccharides of serogroup A, B, C, Y and W-135), pneumococcal antigen (*Streptococcus pnemoniae* type 3 capsular polysaccharide), tuberculosis antigen, cholera antigen (cholera toxin B subunit), staphylococcal antigen (staphylococcal enterotoxin. B), *shigella* antigen (*shigella* polysaccharides), *Borrelia* sp. antigen, *Candida albicans* antigen and *Plasmodium* antigen. The virus derived antigen is exemplified by influenza virus antigen (haemagglutinin and neuraminidase antigens), human papilloma virus (HPV) antigen (glycoprotein), vesicular stomatitis virus antigen (vesicular stomatitis virus glycoprotein), cytomegalovirus, (CMV) antigen, hepatitis virus antigen (hepatitis A (HAV), B (HBV), C(HCV), D (HDV) and G (HGV) antigens) (core antigen and surface antigen), respiratory syncytial virus (RSV) antigen, herpes simplex virus antigen, human immunodeficiency virus (HIV) antigen (GP-120, GP-160, p18, Tat, Gag, Pol, Env) and their complexes. The cancer antigen is selected from the group consisting of Her-2/neu, Proteinase 3, Wilm's Tumor-associated gene (WT-1), murinoglobulin (MUC-1), prostatic acid phosphatase (PAP), prostate-specific antigen (PSA), prostate-specific membrane antigen (PSMA), G250, melanoma antigen (MAGE), B melanoma antigen (BAGE), G melanoma antigen (GAGE), NY-ESO-1 (New York-Esophageal cancer-1), tyrosinase, tyrosinase-related protein-1 (TRP-1), tyrosinase-related protein-2 (TRP-2), gp100 (glycoprotein 100), Melanoma antigen recognized by T cell-1 (MART-1), melanocortin-1 receptor (MCIR), Ig Idiotype, cyclin D-dependent kinase (CDK4), caspase-8, β-catenin, Collagen-induced arthritis (CIA), BCR/ABL, human papillomavirus (HPV) E6/E7, Ebstein-Barr virus (EBV) latent membrane protein 2A (LMP2a), Hepatitis C virus (HCV), Human herpes virus (HHV-8), 5T4, carcinoembryonic antigen (CEA), p53 and α-fetoprotein, but not always limited thereto.

The antigen above can be directly loaded in monocytes or immature myeloid cells (IMCs) as a form of peptide, lipopolysaccharide, polysaccharide, glycoprotein or polynucleotide, or can be introduced into monocytes or immature myeloid cells (IMCs) by being carried on a recombinant virus and then expressed therein. Unlike the cell vaccine loaded with a peptide, the cell vaccine introduced with a whole antigen by the transduction with virus encoding the antigen is not limited to a haplotype of major histocompatibility complex (MHC) and can be applied to everybody and has another advantage of inducing various epitope specific immune responses, particularly inducing humoral immune responses and cell mediated immune responses simultaneously.

The virus introduced into monocytes or immature myeloid cells (IMCs) for the expression of an antigen can be adenovirus, retrovirus, vaccinia virus, Pox virus or Sindbis virus, but not always limited thereto. In addition to using virus, a possible method for delivering the antigen gene is 1) the method wherein DNA is bound to liposome then transfected to protect the DNA from enzymes or absorbed into endosome, 2) the method wherein DNA is bound to molecular conjugate or synthetic ligand composed of proteins to increase DNA transfection efficiency (for example: asialoglycoprotein, transferrin and polymeric IgA], 3) the method using new DNA transfection system with PTD (Protein transduction domain) wherein antigen gene is transmitted owing to the increased DNA transfection efficiency to cells (for example: Mph-1), and 4) the method wherein a peptide or antigen protein is loaded in monocytes or immature myeloid cells (IMCs).

The vaccine of the present invention can additionally include, in addition to the natural killer T cell ligand and monocytes or IMCs, one or more effective ingredients having the same or similar effect with them. The vaccine can also include, in addition to the above-mentioned effective ingredients, one or more pharmaceutically acceptable carriers for the administration. The pharmaceutically acceptable carrier can be selected or be prepared by mixing more than one ingredients selected from the group consisting of saline, Ringer's solution, buffered saline, dextrose solution, maltodextrose solution, glycerol and ethanol. Other general additives such as anti-oxidative agent, buffer solution, bacteriostatic agent, etc., can be added. In order to prepare injectable solutions such as aqueous solution, suspension and emulsion, diluents, dispersing agents, surfactants, binders and lubricants can be additionally added. The vaccine of the present invention can further be prepared in suitable forms for each disease or according to ingredients by following a method represented in Remington's Pharmaceutical Science (the newest edition), Mack Publishing Company, Easton Pa.

The vaccine of the present invention can be administered by parenterally and the parenteral administration includes subcutaneous injection, intravenous injection, intramuscular injection and intrathoracic injection. To prepare the vaccine as a formulation for parenteral administration, monocytes or IMCs loaded with the natural killer T cell ligand, monocytes or IMCs loaded with the natural killer T cell ligand and a peptide or monocytes or IMCs transduced with a virus expressing a tumor antigen and loaded with the natural killer T cell ligand are mixed with a stabilizer or a buffering agent to produce a solution or suspension, which is then formulated as ampoules or vials.

The vaccine of the present invention can be prepared in various forms according to the administration pathways. For example, the vaccine of the invention can be formulated as sterilized aqueous solutions or dispersions for injection, or as freeze-dried preparations. The freeze-dried vaccine is typically stored at 4° C. and can be recovered by using stabilizing solution such as saline or/and HEPES containing or not containing supplements.

In a preferred embodiment of the present invention, factors that might affect the determination of dose of the vaccine are administration method, administration frequency, specific disease under treatment, severity of disease, clinical history, other treatment agents being used, and personal features such as age, height, weight, health and body conditions. In general, as the weight of a patient under treatment increases, the dose of the composition is preferably increased.

The vaccine can be administered by effective dose to induce immune responses in a patient. For example, the vaccine can be administered to human once or a few times a day by the dosage of $1 \times 10^3 \sim 1 \times 10^9$ cells/kg, and more preferably $1 \times 10^4$ cells/kg~$1 \times 10^8$ cells/kg. To prepare αGalCer loaded monocyte or IMC vaccine, a medium has to be supplemented with αGalCer at the concentration of 1~2 μg/ml per $1 \times 10^6 \sim 1 \times 10^7$ cells/ml. To prepare αGalCer and peptide co-loaded monocyte or IMC vaccine, a medium has to be supplemented with αGalCer at the concentration of 1~2 μg/ml per $1 \times 10^6 \sim 1 \times 10^7$ cells/ml and peptide at the concentration of 1~10 μg/ml per $1 \times 10^6 \sim 1 \times 10^7$ cells/ml.

αGalCer doesn't seem to induce toxicity in rodents and apes (Nakata et al., *Cancer Res* 58:1202-1207, 1998). No side effects have been reported when 2200 μg/kg of αGalCer was administered into a mouse (Giaccone et al., *Clin Cancer Res* 8:3702, 2000). From the clinical trials, a light headache has been reported as a side effect according to the systemic administration of αGalCer (Mie Nieda et al., *Blood* 103: 383-389, Giaccone et al., *Clin Cancer Res* 8:3702, 200), which can be prevented by the administration of paracetamol. There is a little, if ever, chance to show a slight systemic side effect (Giaccone et al., *Clin Cancer Res* 8:3702, 2002).

The present invention also provides a natural killer T cell activator mediated by αGalCer loaded monocytes or IMCs.

As explained hereinbefore, αGalCer-loaded monocytes or IMCs of the present invention, like αGalCer-loaded dendritic cells, activate iNKT cells in vivo which could induce anticancer immunity. Therefore, αGalCer-loaded monocytes or IMCs of the present invention can be used as a natural killer T cell activator just as αGalCer-loaded dendritic cells can be.

The present invention also provides a cytotoxic response inducer comprising monocytes or IMCs expressing tumor antigen.

Figure 8:
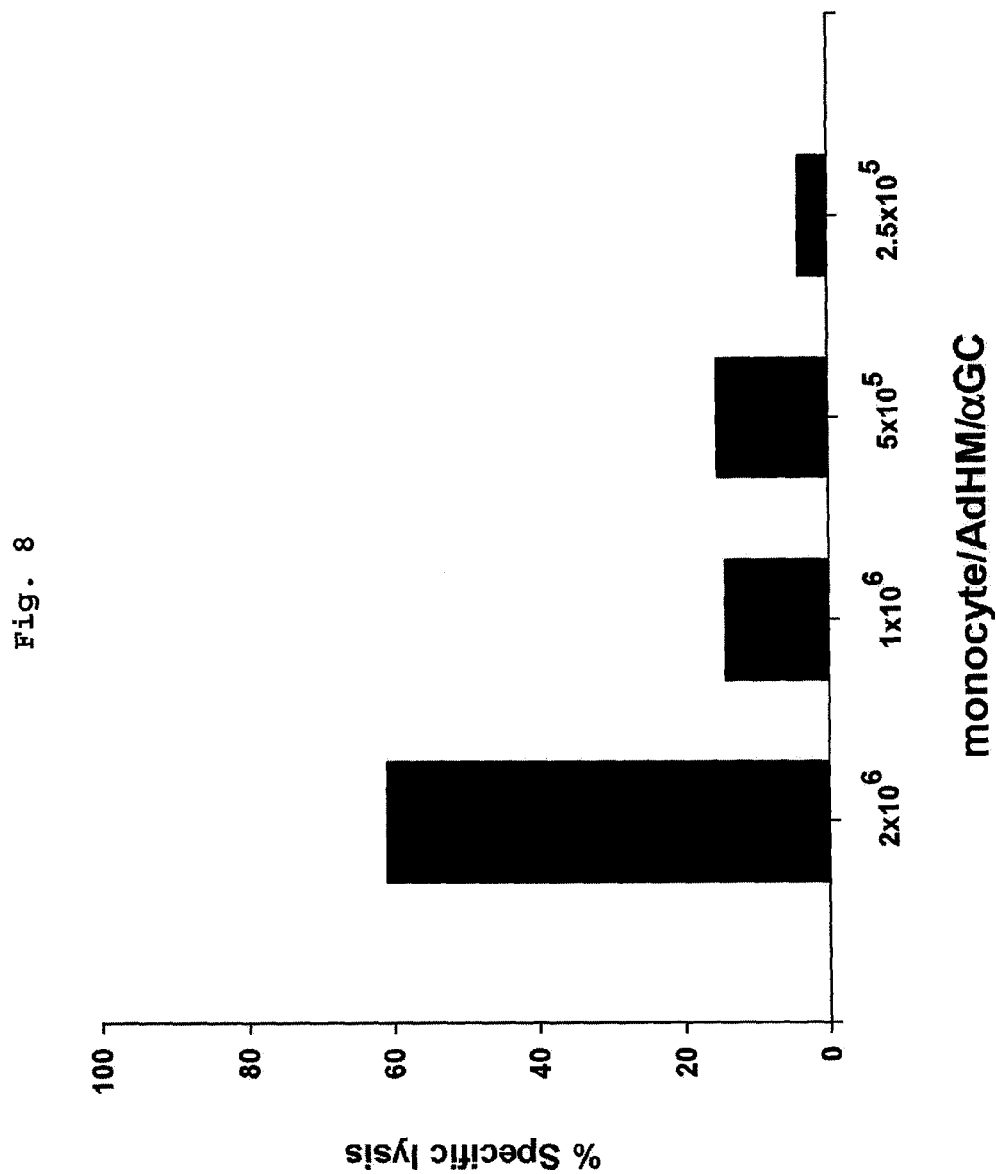
FIG. 8 is a diagram illustrating the activity of antigen peptide-specific cytotoxic T lymphocytes induced by monocyte vaccine loaded with αGalCer and transduced with adenovirus expressing an antigen.
Figure 10:
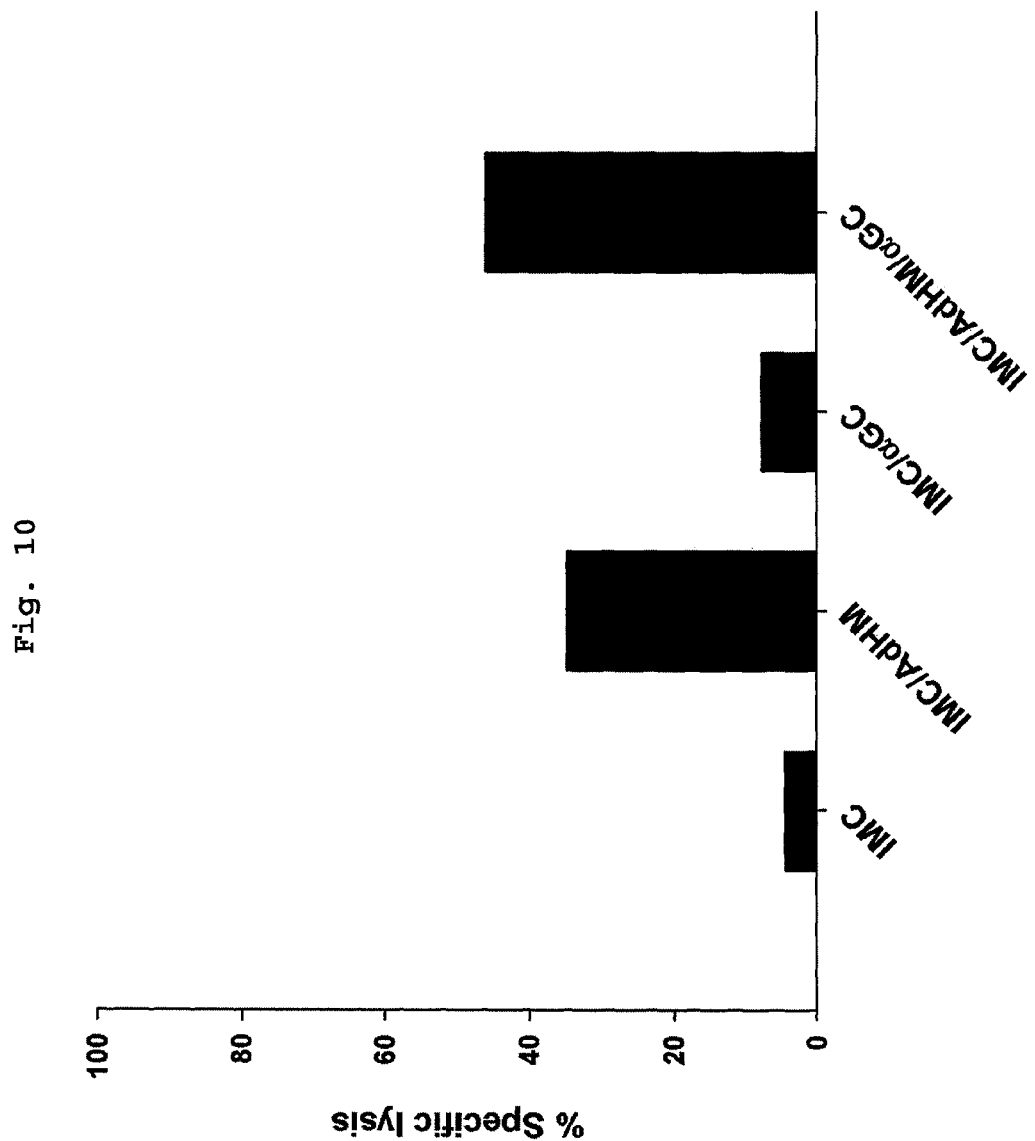
FIG. 10 is a diagram illustrating the activity of antigen peptide-specific cytotoxic T lymphocytes induced by IMC vaccine loaded with αGalCer and an antigen peptide.
Figure 12:
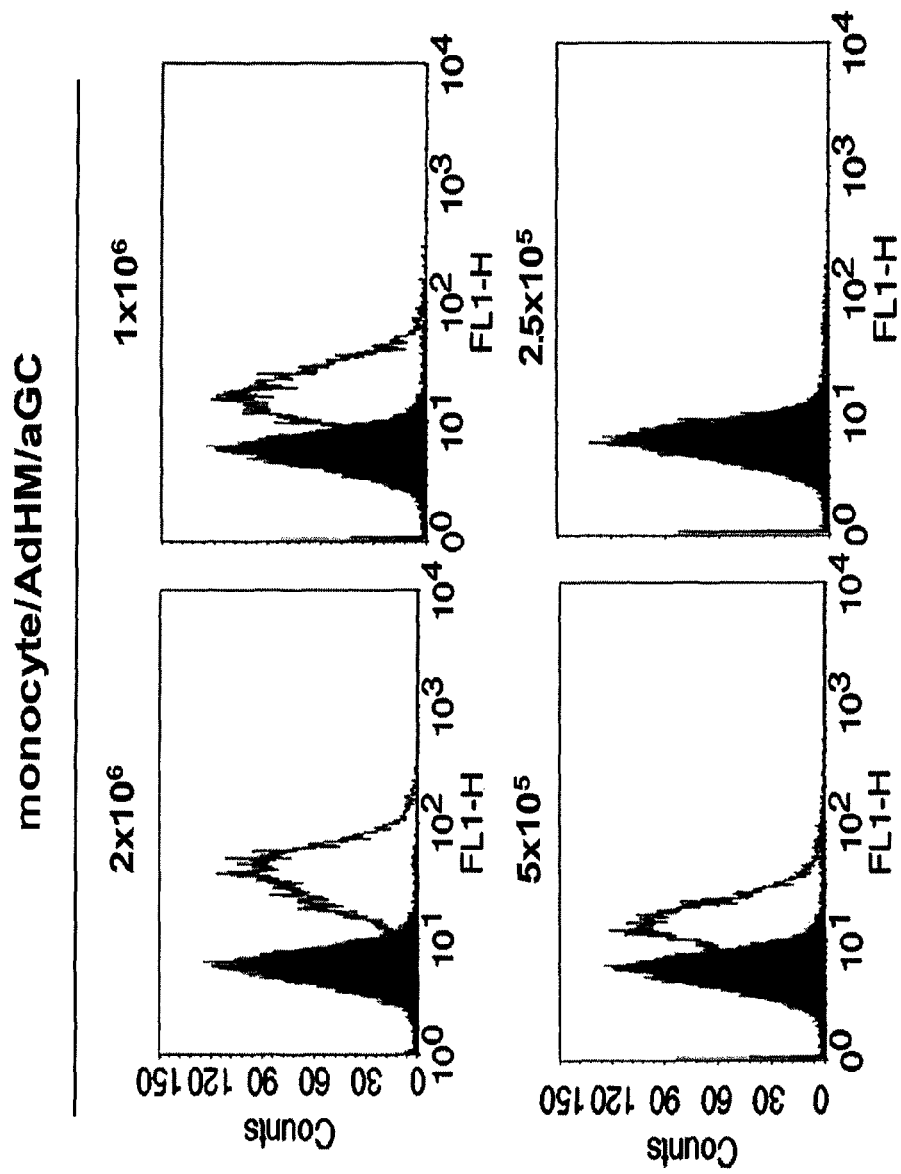
FIG. 12 is a diagram illustrating the antigen specific antibody reaction induced by monocyte loaded with αGalCer and transduced with adenovirus expressing an antigen.

Unlike the monocyte or IMC vaccine was loaded with a peptide to induce cell-mediated immune response, the monocyte or IMC vaccine transduced with adenovirus can induce both cell-mediated immune responses and humoral immune responses simultaneously (see FIGS. 8, 10 and 12).

The present invention also provides a method for the prevention and immunotherapy for diseases comprising the step of administering the immunotherapeutic and prophylactic vaccine comprising monocytes or immature myeloid cells (IMCs) loaded with the ligand of natural killer T cell and an antigen to a subject.

The applicable subject of the present invention is vertebrates and preferably mammals, and more preferably such experimental animals as rat, rabbit, guinea pig, hamster, dog, cat, etc, and most preferably apes such as chimpanzee and gorilla, but not always limited thereto.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Anticancer Activity of Monocyte Vaccine Loaded with αGalcer and an Antigen

Monocytes are immature precursor cells originated from bone marrow that have potential for being differentiated into dendritic cells (DC) or macrophages. In this invention, it was investigated whether monocytes, the precursors of dendritic cells or macrophages, have antigen specific anticancer effect assisted by natural killer T cells.

<1-1> Anticancer Activity of Monocyte Vaccine Loaded with αGalcer and an Antigen Peptide Monocytes were isolated from BALB/c mice.

Particularly, peripheral blood mononuclear cells (PB-MCs) and the spleen were isolated from BALB/c mice (Orient, Korea), followed by homogenization. Granulocytes and red blood cells (RBCs) were removed by Ficoll (Sigma, USA) density gradient centrifugation. After depleting $B220^+$ and $CD11c^+$ cells using anti-B220 (Miltenyibiotec, Germany) and anti-CD11c microbeads (Miltenyibiotec, Germany), the present inventors isolated $CD11b^+$ cells using anti-CD11b microbeads (Miltenyibiotec, Germany).

The monocytes separated and purified by the above method were cultured in a $CO_2$ incubator along with αGalCer (1.5 μg/ml) or vehicle (0.5% Tween in PBS) for 14 hours. 2.5 μg/ml of Her-2/$neu_{63-71}$ (Anygen, Korea), the epitope peptide of cytotoxic T lymphocyte, was added in the cell culture media for additional 1 hour, which was loaded in the $H-2K^d$ on the monocytes. The unloaded peptide was washed off. As a result, monocyte vaccine was prepared.

The anticancer effect of the monocyte vaccine loaded with αGalCer and/or an antigen peptide was investigated by using Her-2/CT26 (Penichet M L et al., *Lab Anim Sci* 49:179-88, 1999), the cancer cell line expressing tumor associated antigen, Her-2/neu.

First, HER-2/CT26 cells were transplanted in BALB/c mice ($2 \times 10^5$ cells/mouse) by intravenous injection. On the next day, monocyte/pep (loaded with an antigen peptide alone), monocyte/αGC (loaded with αGalCer alone) and monocyte/pep/αGC (loaded with both αGalCer and the antigen peptide) were administered respectively. Then, the survival periods were compared.

As a result, the survival period of the group treated with monocyte/pep was as long as the survival period of the control group challenged with cancer cell only (by intravenous injection). But, the survival period of the group treated with monocyte/αGC was extended a little. In the meantime, the survival period of the group administered with monocyte/pep/αGC was significantly extended, suggesting that the vaccine had anticancer effect (FIG. 1).

<1-2> Anticancer Activity of Monocyte Vaccine Loaded with αGalcer and Transduced with Adenovirus Expressing an Antigen The monocytes separated and purified by the same manner as described in Example <1-1> were tranduced with adenovirus containing the gene encoding Her-2/neu extracellular domain and transmembrane domain (AdHM; Viromed Co., Ltd., Korea) in a serum-free medium for 90 minutes in a $CO_2$ incubator by 100 MOI (multiplicity of infection). Serum was added thereto and αGalCer (1.5

μg/ml) or vehicle (0.5%. Tween in PBS) was also added and incubated for an additional 14 hours. As a result, monocyte vaccine was prepared.

The anticancer effect of the monocyte vaccine loaded with αGalCer and/or transduced with adenovirus expressing an antigen was investigated by the same manner as described in Example <1-1> by using HER-2/CT26.

First, HER-2/CT26 cells were transplanted in BALB/c mice ($2 \times 10^5$ cells/mouse) by intravenous injection. On the next day, monocyte/AdHM (transduced with adenovirus expressing an antigen), monocyte/αGC (loaded with αGalCer alone) and monocyte/AdHM/αGC (loaded with αGalCer and transduced with adenovirus expressing an antigen) were administered respectively. Then, the survival periods were compared.

Figure 2:
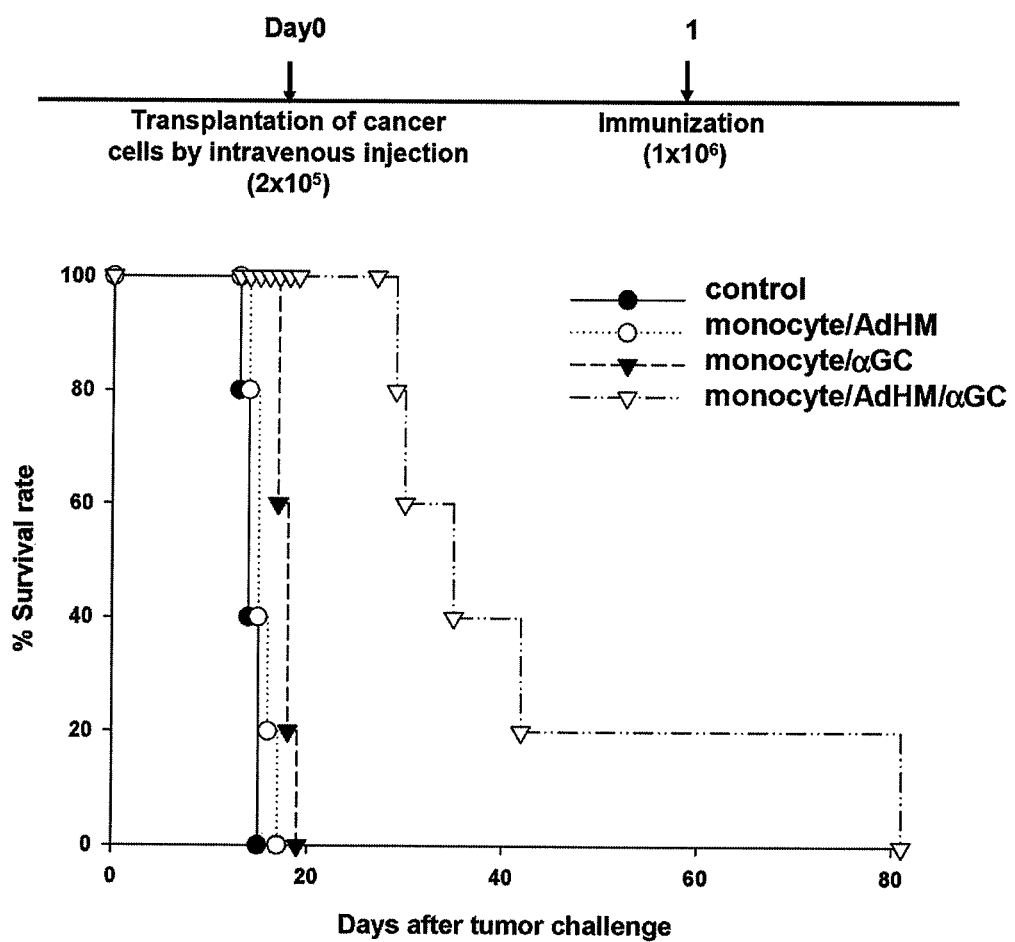
FIG. 2 is a diagram illustrating the anticancer effect of monocyte vaccine loaded with αGalCer and transduced with adenovirus expressing an antigen.

As a result, the survival period of the group treated with monocyte/AdHM was as long as the survival period of the control group challenged with cancer cell only (by intravenous injection). But, the survival period of the group treated with monocyte/αGC was extended a little. In the meantime, the survival period of the group administered with monocyte/AdHM/αGC was significantly extended, suggesting that the vaccine had anticancer effect (FIG. 2).

Example 2

Anticancer Activity of Immature Myeloid Cell (IMC) vaccine loaded with αGalcer and an Antigen <2-1> Anticancer Activity of IMC Vaccine Loaded with αGalcer and an Antigen Peptide Immature myeloid cells (IMCs) were isolated from BALB/c mice.

HER-2/CT26 cells were transplanted subcutaneously in BALB/c mice. 4 weeks later, when the tumor volume was grown to at least 1500 mm$^3$, spleens were isolated from the mice, followed by homogenization. B220+ B cells or CD11c+ dendritic cells were eliminated by using anti-B220 microbeads (Miltenyibiotec, Germany) and anti-CD11c microbeads (Miltenyibiotec, Germany).

These cells were incubated in a $CO_2$ incubator for 14 hours in αGalCer (1.5 μg/ml) containing media, vitamin A (ATRA, all trans-retinoic acid, 20 μM; Sigma, USA), GM-CSF (granulocyte macrophage colony-stimulating factor, 20 ng/ml; R&D systems, USA) or vehicle (0.5% Tween in PBS; Sigma, USA). CD11b+ cells were obtained therefrom by using anti-CD11b microbeads (Miltenyibiotec, Germany). Then, 2.5 μg/ml of Her-2/neu$_{63-71}$ (Anygen, Korea) peptide was loaded thereto for one hour. As a result, IMC vaccine was prepared.

The anticancer effect of the IMC vaccine loaded with αGalCer and/or an antigen peptide was investigated by using Her-2/CT26.

First, HER-2/CT26 cells were transplanted in BALB/C mice ($2 \times 10^5$ cells/mouse) by intravenous injection. On the next day, IMC/pep (loaded with an antigen peptide alone), IMC/pep/ATRA (loaded with an antigen peptide and incubated in vitamin A containing media), IMC/pep/GM-CSF (loaded with an antigen peptide and incubated in GM-CSF containing media) and IMC/pep/αGC (loaded with αGalCer and an antigen peptide) were administered respectively. Then, the survival periods were compared.

As a result, the survival period of the group treated with IMC/pep or IMC/pep/ATRA was as long as the survival period of the control group challenged with cancer cell only (by intravenous injection). But, the survival period of the group treated with IMC/pep/GM-CSF was extended a little.

Figure 3:
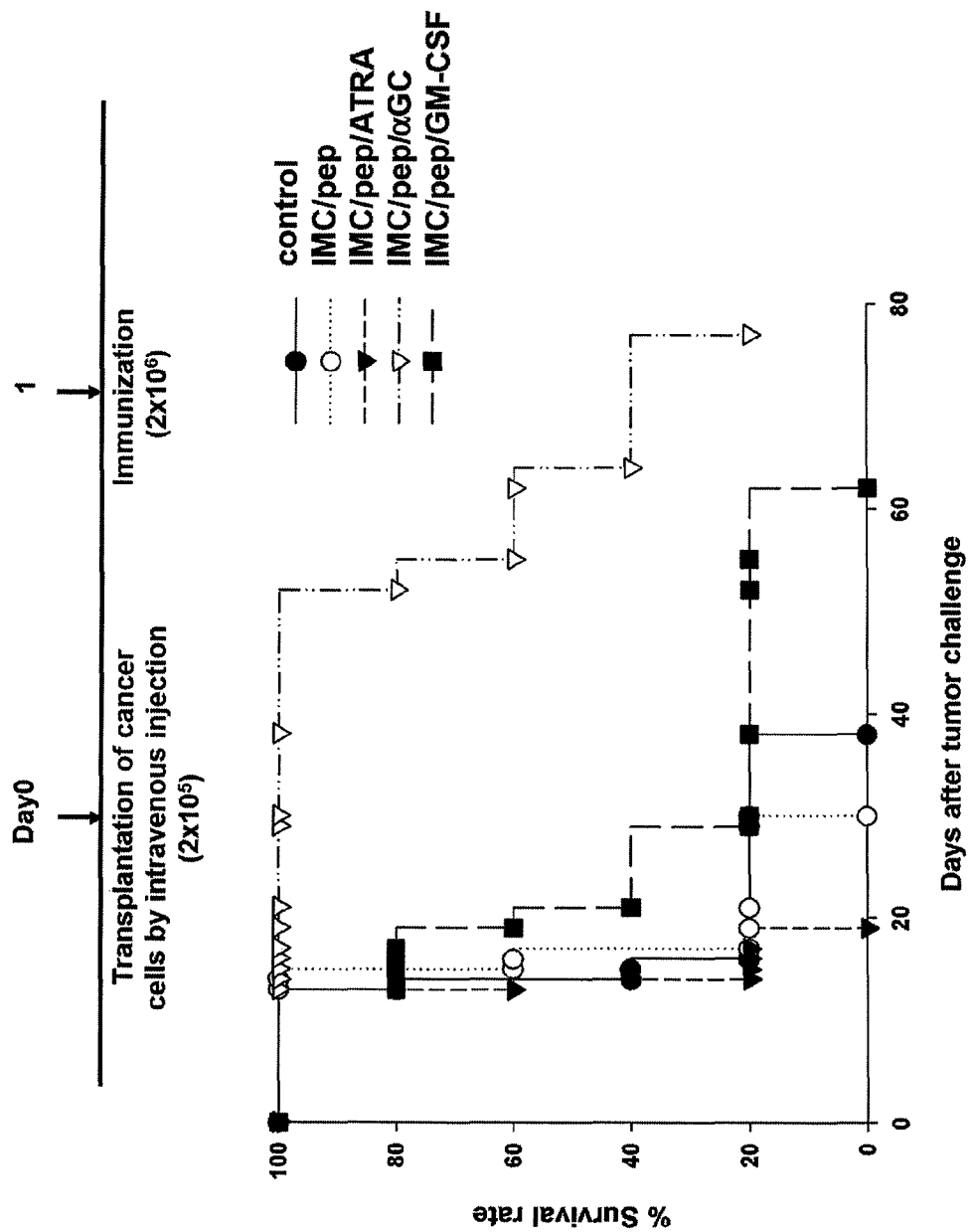
FIG. 3 is a diagram illustrating the anticancer effect of IMC vaccine loaded with αGalCer and an antigen peptide.

In the meantime, the survival period of the group administered with IMC/pep/αGC was significantly extended, suggesting that the vaccine had anticancer effect (FIG. 3).

<2-2> Anticancer Activity of IMC Vaccine Loaded with αGalcer and Transduced with Adenovirus Expressing an Antigen IMC vaccine loaded with αGalCer and transduced with adenovirus expressing an antigen was prepared.

The immature myeloid cells (IMCs) separated and purified by the same manner as described in Example <2-1> were infected with adenovirus expressing an antigen in a serum-free medium for 60 minutes in a $CO_2$ incubator by 100 MOI. Then, serum was supplemented thereto, followed by further culture for 5 hours to prepare IMC vaccine.

HER-2/CT26 cells were transplanted in BALB/c mice ($2 \times 10^5$ cells/mouse) by intravenous injection. On the next day, IMC, IMC/AdHM (transduced with adenovirus expressing an antigen) and IMC/AdHM/αGC (loaded with αGalCer and transduced with adenovirus expressing an antigen) were administered respectively. Then, the survival periods were compared.

Figure 4:
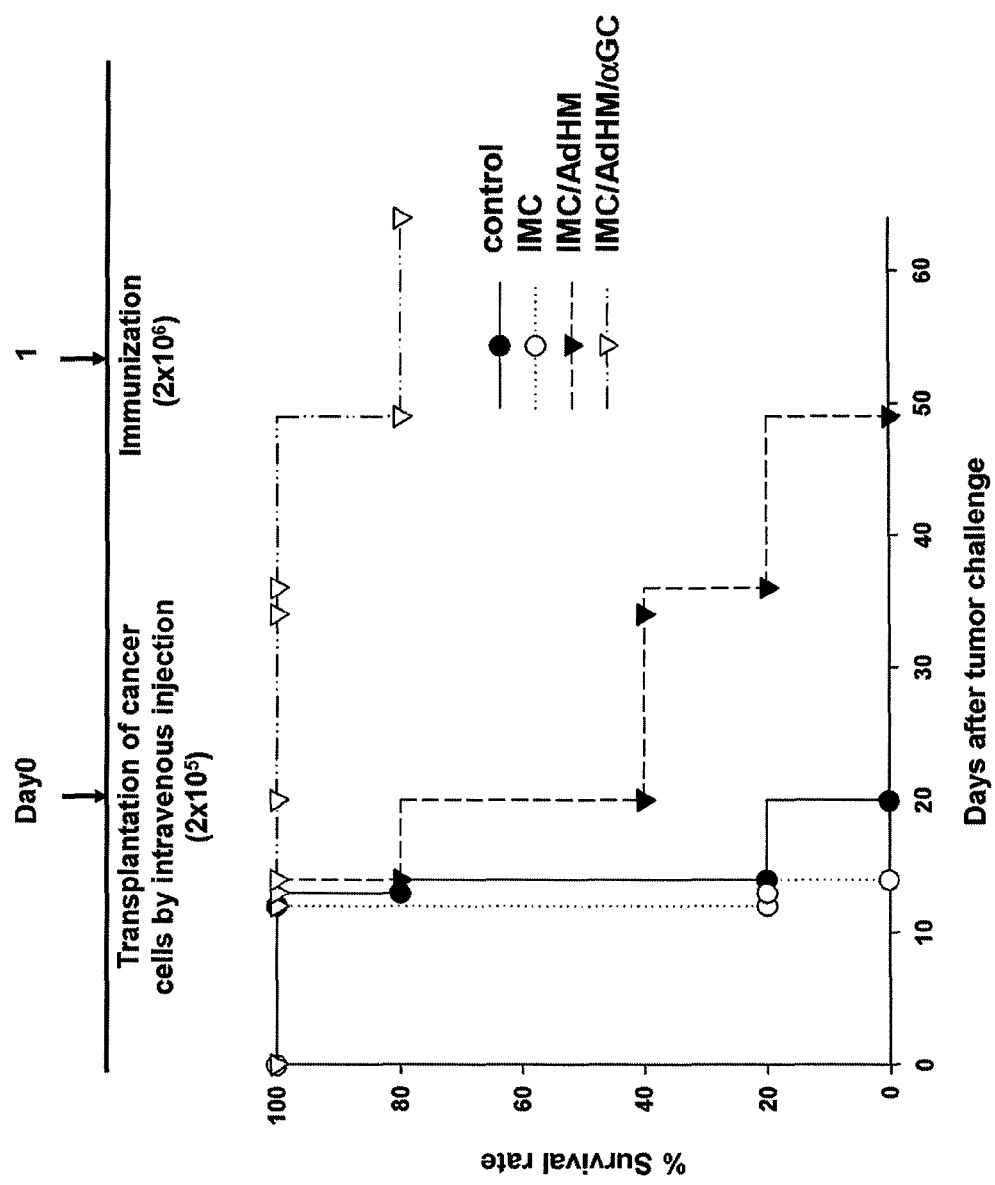
FIG. 4 is a diagram illustrating the anticancer effect of IMC vaccine loaded with αGalCer and transduced with adenovirus expressing an antigen.

As a result, the survival period of the group treated with IMC/AdHM was a little extended, whereas the survival period of the group treated with IMC/AdHM/αGC was significantly extended, indicating that the vaccine had excellent anticancer effect (FIG. 4).

Example 3

Required Immune Cells to Induce Anticancer Activity by IMC Vaccination

The subsets of anticancer immune cells activated by the IMC vaccination were investigated.

To eliminate immune cells, BALB/c mice were treated with the immune cell eliminating antibodies [anti-CD4 eliminating antibody: GK1.5 hybridoma (ATCC, USA), anti-CD8 eliminating antibody: 2.43 hybridoma (ATCC, USA), anti-NK eliminating antibody: α-asialoGM1 antibody (Wako, USA)] by intraperitoneal injection at 4 days intervals from a day before HER-2/CT26 cancer cells were transplanted into the BALB/c mice by intravenous injection. One day after the cancer cell injection, the mice were administered with the IMC/AdHM/αGC vaccine prepared by the same manner as described in Example <2-2> by intravenous injection. The survival periods were compared.

Figure 5:
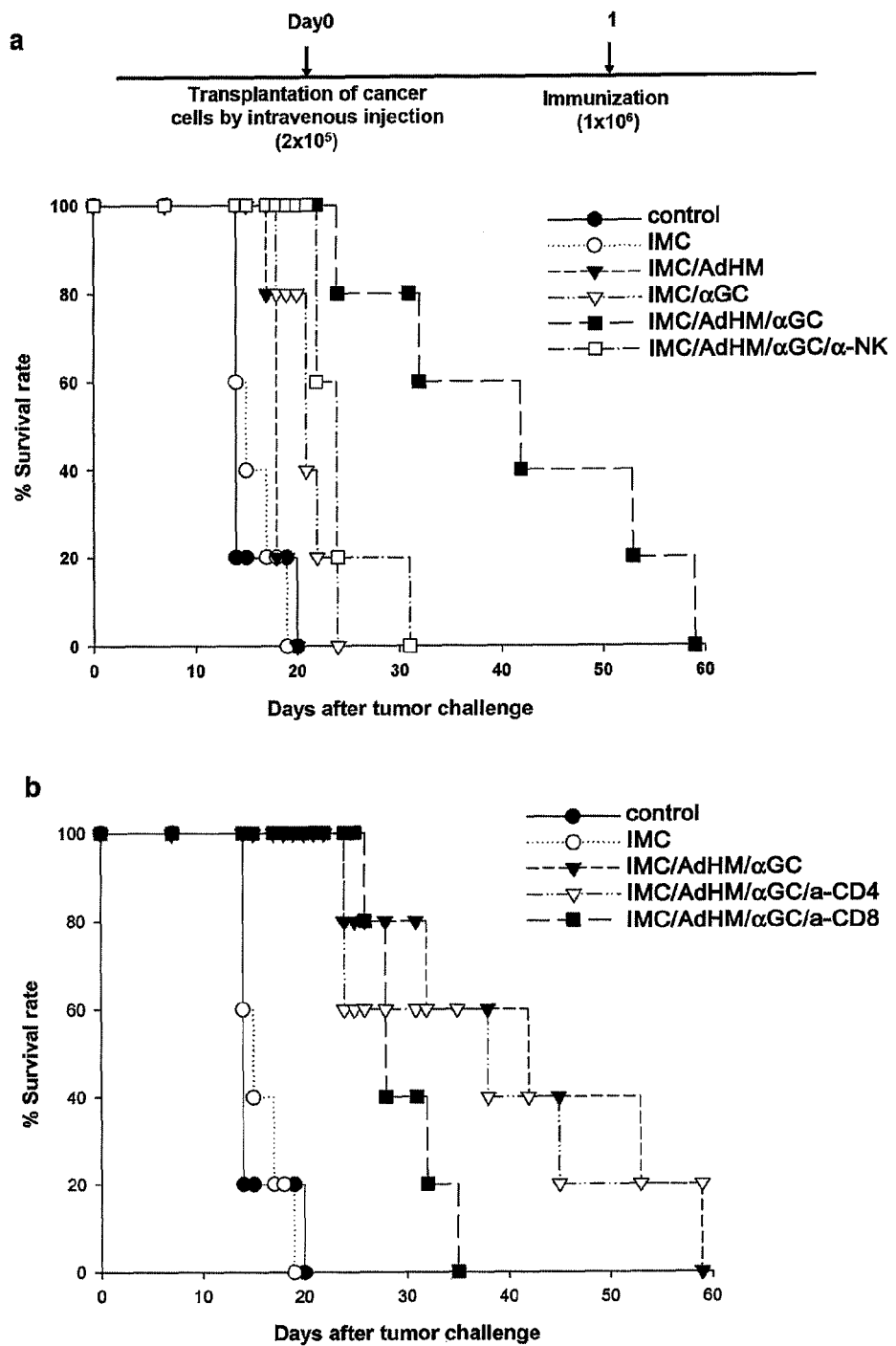
FIG. 5 is a diagram illustrating the confirmation of immune cells having anticancer effect by IMC vaccine:
  a: NK cell elimination; and,
  b: CD4 or CD8 cell elimination.

As a result, the survival period of the NK deficient group (IMC/AdHM/αGC/a-NK) was similar with that of the control group challenged with cancer cell only, suggesting that NK cells are important immune cells playing a certain role in anticancer activity induced by IMC vaccination (FIG. 5a). The survival period of the CD8+ T cell deficient group (IMC/AdHM/αGC/a-CD8) was significantly reduced, compared with the normal immunized group (IMC/AdHM/αGC), suggesting that the anticancer effect induced by IMC vaccination is mediated by the CD8+ T cells (FIG. 5b). However, the survival period of the CD4+ T cell deficient group (IMC/AdHM/αGC/a-CD4) was a little extended or similar with that of the normal immunized group (IMC/AdHM/αGC), indicating that the CD4+ cells are dispensable to induce anticancer effect by IMC vaccination (FIG. 5b).

Example 4

Activation of Antigen Specific Cytotoxic T Lymphocytes by Monocyte Vaccine Loaded with αGalcer and an Antigen To investigate whether the monocyte vaccine could activate antigen peptide-specific cytotoxic T lymphocytes to induce cytotoxic immune response, in vivo CTL assay was performed.

<4-1> Activation of Antigen Peptide-Specific Cytotoxic T Lymphocytes by Monocyte Vaccine Loaded with αGalcer and an Antigen Peptide To investigate whether the monocyte vaccine could activate antigen peptide-specific cytotoxic T lymphocytes to induce cytotoxic immune response, in vivo CTL assay was performed.

Particularly, BALB/c mice were immunized with the monocytes, monocyte/pep or monocyte/pep/αGC prepared by the same manner as described in Example <1-1>. Nine days later, cytotoxic assay was performed. First, splenocytes from the syngenic naive mice were divided into two groups: one group was loaded with Her-2/neu$_{63-71}$ peptide (2.5 μg/ml) and labeled with 20 μM CFSE (carboxyfluorescein diacetate succinimidyl ester, Invitrogen, USA) (CFSE$^{high}$) and the other group was labeled with 2.5 μM CFSE without peptide loading (CFSE$^{low}$, used as a control). Equal amounts of the two group cells were mixed and administered to the immunized mice. On the next day, the CFSE$^{high}$ and CFSE$^{low}$ cell populations in splenocytes were analyzed by flow cytometry. The lower the percentage of the CFSE$^{high}$ cells was, the higher the cytotoxic immune response was.

Immunization was also performed with different cell concentrations of monocyte/pep/αGC vaccine (5×10$^6$, 1×10$^6$, 2×10$^5$ and 4×10$^4$). Nine days later, in vivo CTL assay was performed by the same manner as described above.

Figure 6:
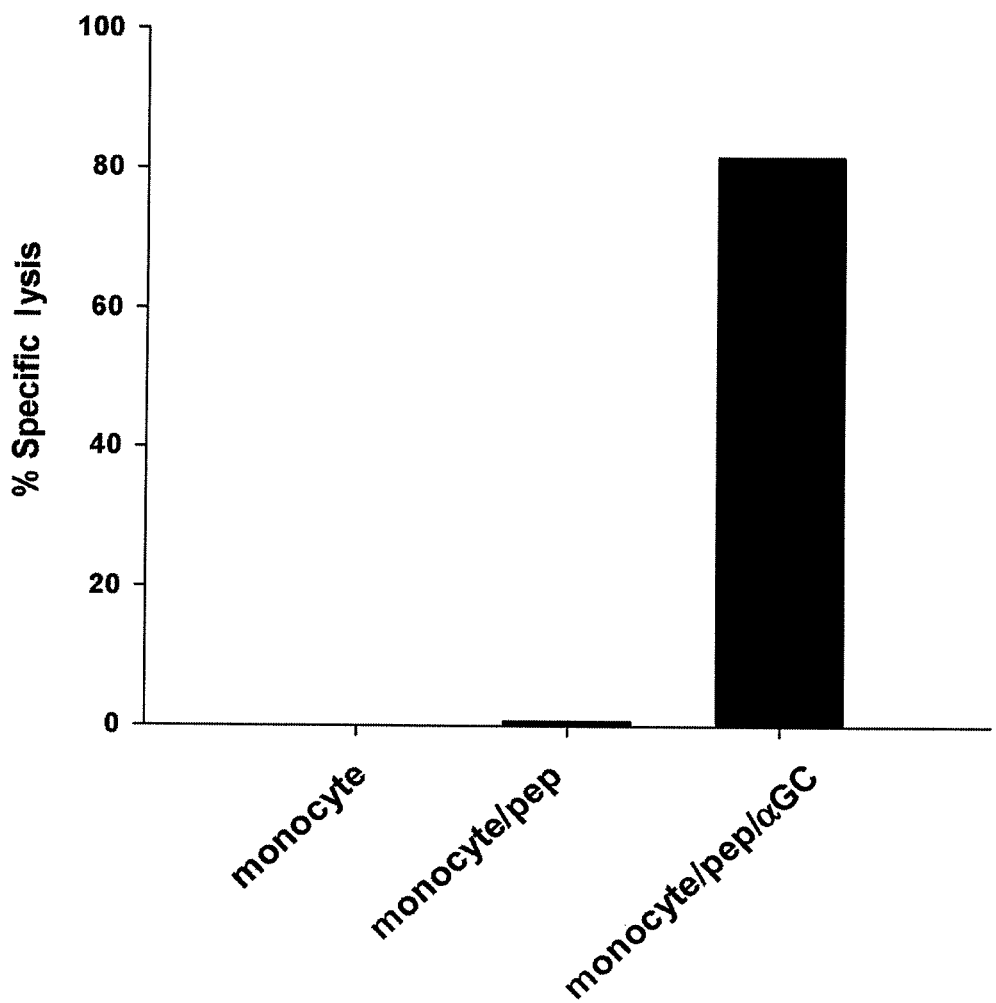
FIG. 6 is a diagram illustrating the activity of antigen peptide-specific cytotoxic T lymphocytes induced by monocyte vaccine loaded with αGalCer and an antigen peptide.
Figure 7:
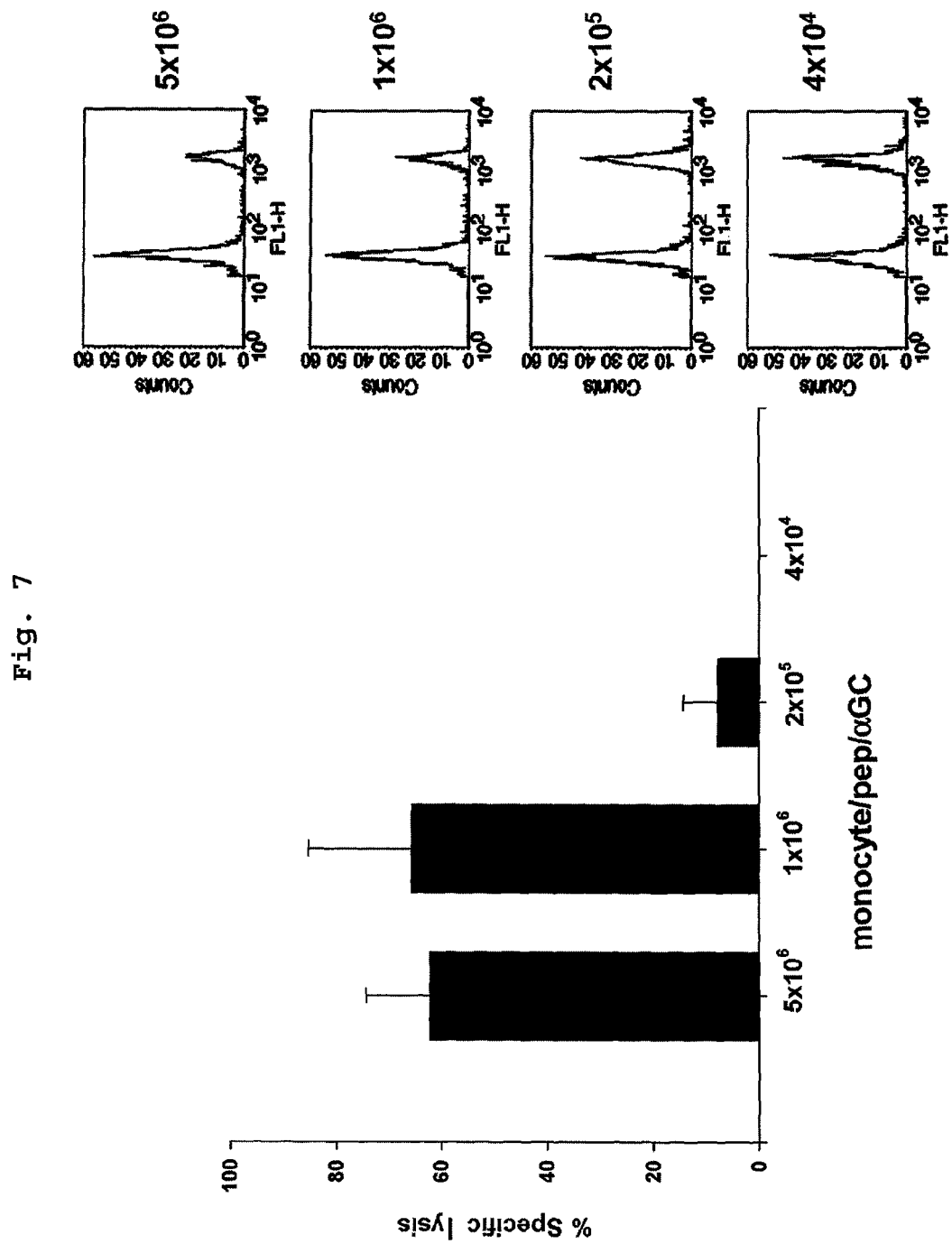
FIG. 7 is a diagram illustrating the dose-dependent activity of antigen peptide-specific cytotoxic T lymphocytes induced by monocyte vaccine loaded with αGalCer and an antigen peptide.

As a result, cytotoxic immune responses was hardly detected in the groups each treated with monocytes alone and monocyte/pep, while destruction of the target loaded with peptide was detected in the group treated with monocyte/pep/αGC (FIG. 6). In vivo CTL assay was performed with different cell concentrations of monocyte/pep/αGC vaccine by the same manner as described above. As a result, only 1×10$^6$ cells induced cytotoxic immune response effectively (FIG. 7).

<4-2> Activation of Antigen Peptide-Specific Cytotoxic T Lymphocytes by Monocyte Vaccine Loaded with αGalcer and Transduced with Adenovirus Expressing an Antigen To investigate whether the monocyte vaccine loaded with αGalCer and transduced with adenovirus expressing an antigen could activate peptide-specific cytotoxic T lymphocytes to induce cytotoxic immune response, in vivo CTL assay was performed.

Particularly, BALB/c mice were immunized with monocyte/AdHM/αGC vaccine prepared by the same manner as described in Example <1-2> at different cell concentrations of 2×10$^6$, 1×10$^6$, 5×10$^5$ and 2.5×10$^5$. Ten days later, in vivo CTL assay was performed by the same manner as described in Example <4-1>.

As a result, effective cytotoxic immune response was detected in the mice immunized with 2×10$^6$ cells of the monocyte vaccine. However, when the immunization was performed with less than 1×10$^6$ cells, cytotoxic immune response was slightly detected (FIG. 8), which was lower than cytotoxic immune response induced by monocyte/pep/αGC vaccine. But, in terms of anticancer effect, the survival period of the group was extended, compared with that of the group treated with monocyte/pep/αGC vaccine. The above results suggest that the adenovirus vaccine induces not only cytotoxic T cell response but also other immune responses.

Example 5

Activation of Antigen Specific Cytotoxic T Lymphocytes by IMC Vaccine Loaded with αGalcer and an Antigen To investigate whether the IMC vaccine could activate antigen peptide-specific cytotoxic T lymphocytes, in vivo CTL assay was performed.

<5-1> Activation of Antigen Peptide-Specific Cytotoxic T Lymphocytes by IMC Vaccine Loaded with αGalcer and an Antigen Peptide To investigate whether the IMC vaccine could activate antigen peptide-specific cytotoxic T lymphocytes, in vivo CTL assay was performed.

Particularly, BALB/c mice were immunized with IMC/pep, IMC/pep/αGC, IMC/pep/ATRA or IMC/pep/GM-CSF prepared by the same manner as described in Example <2-1>. Ten days later, in vivo CTL assay was performed by the same manner as described in Example <4-1>.

Figure 9:
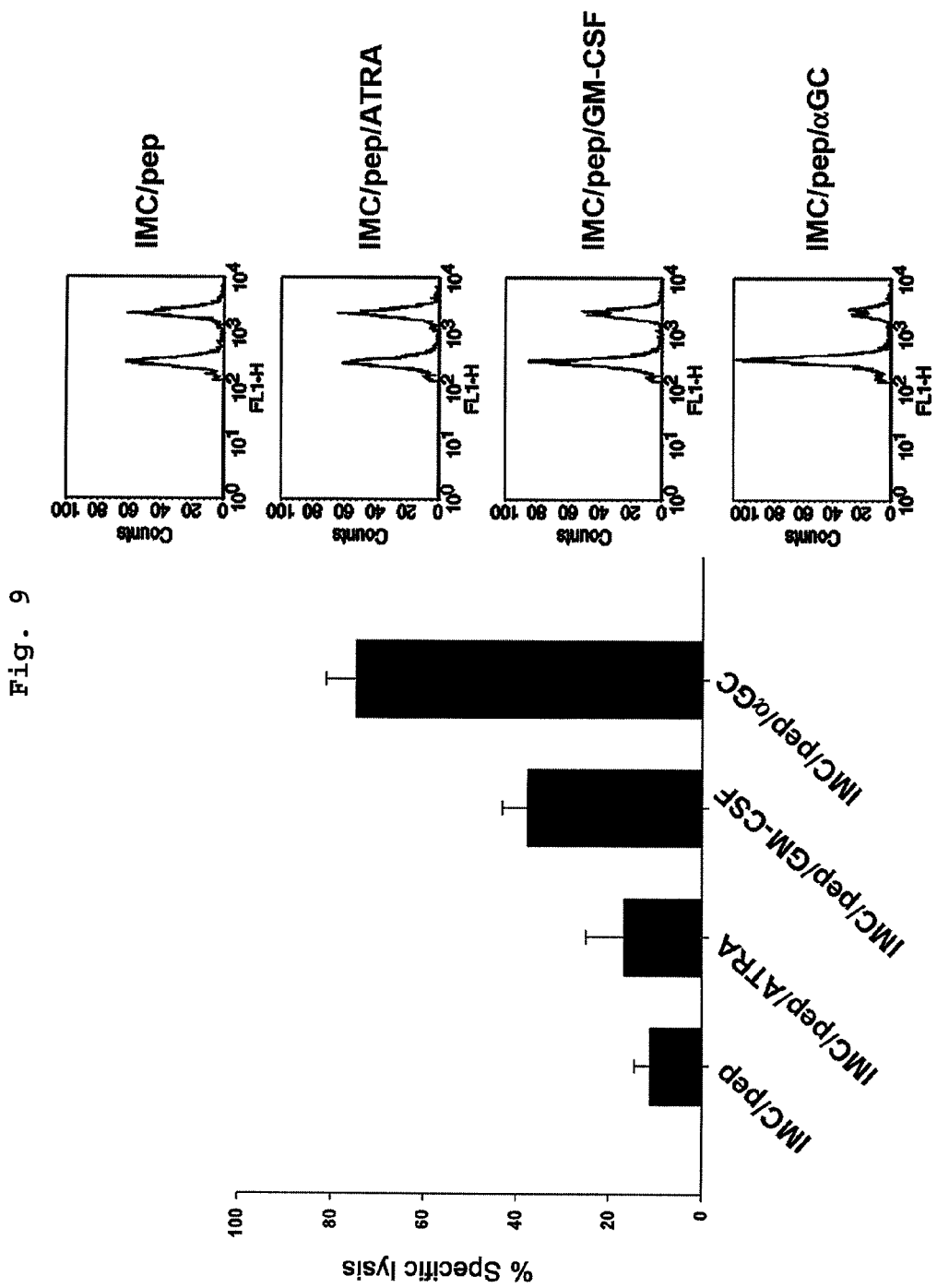
FIG. 9 is a diagram illustrating the dose-dependent activity of antigen peptide-specific cytotoxic T lymphocytes induced by IMC vaccine loaded with αGalCer and an antigen peptide.

As a result, low level of cytotoxic immune responses were detected in the groups treated with IMC/pep and with IMC/pep/ATRA, while a little higher cytotoxic immune response was detected in the group treated with IMC/pep/GM-CSF. However, the group treated with IMC/pep/αGC vaccine induced high level of cytotoxic immune response (FIG. 9). The above results indicate that the IMC/pep/αGC vaccine induced antigen specific cytotoxic immune response effectively enough to destroy target cells, suggesting that the vaccine had excellent anticancer effect as described in Example <2-1>.

<5-2> Activation of Antigen Peptide-Specific Cytotoxic T Lymphocytes by IMC Vaccine Loaded with αGalcer and Transduced with Adenovirus Expressing an Antigen To investigate whether the IMC vaccine could activate antigen peptide-specific cytotoxic T lymphocytes to induce cytotoxic immune response, in vivo CTL assay was performed.

Particularly, BALB/c mice were immunized with IMC, IMC/AdHM, IMC/αGC or IMC/AdHM/αGC prepared by the same manner as described in Example <2-2>. Ten days later, in vivo CTL assay was performed by the same manner as described in Example <4-1>.

And, BALB/c mice were immunized with IMC/AdHM/αGC vaccine at different cell concentrations of 8×10$^6$, 2×10$^6$, 5×10$^5$ and 1.25×10$^5$. Ten days later, in vivo CTL assay was performed by the same manner as described in Example <4-1>.

As a result, cytotoxic immune response was significantly increased in the group treated with IMC/AdHM, compared with the groups treated with IMC alone and IMC/αGC, and cytotoxic immune response was more significantly increased in the group treated with IMC/AdHM/αGC (FIG. 10). The level was not so high as the result from the treatment of the peptide loaded cellular vaccine of Example <5-1>, which seems to be because that the peptide loaded cellular vaccine was only loaded with CD8+ T cell epitope, whereas the cell vaccine transduced with virus comprising a whole antigen does not express specific single epitope only, and because that the transduction efficiency is not complete, resulting in the comparatively a low level of antigen peptide-specific cytotoxic immune response.

Figure 11:
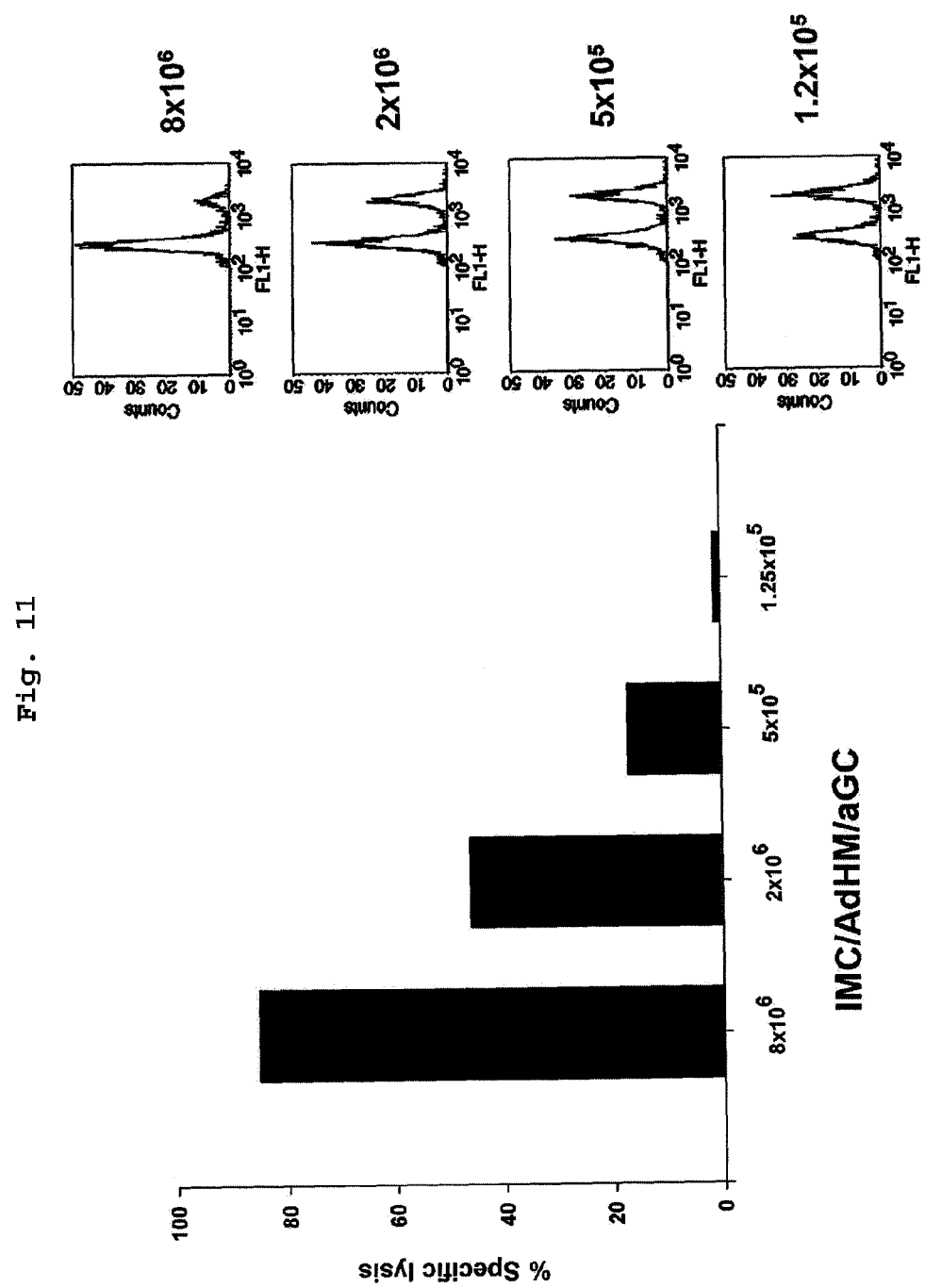
FIG. 11 is a diagram illustrating the dose-dependent activity of antigen peptide-specific cytotoxic T lymphocytes induced by IMC vaccine loaded with αGalCer and transduced with adenovirus expressing an antigen.

In vivo CTL assay was performed again with different cell concentrations of IMC/AdHM/αGC vaccine. As a result, when immunization was performed with 8×10⁶ cells, cytotoxic immune response approaching 90% was detected, indicating that the IMC/AdHM/αGC vaccine effectively induced antigen specific cytotoxic immune response (FIG. 11).

Example 6

Antigen Specific Antibody Response Induced by Monocyte Vaccine Loaded with αGalcer and Transduced with Adenovirus Expressing an Antigen To investigate whether the monocyte vaccine transduced with adenovirus expressing an antigen could induce both cell mediated immune responses and humoral immune responses, Her-2/neu specific antibody production by the monocyte vaccine tranduced with AdHM was examined.

Precisely, BALB/c mice were administered with monocyte/AdHM/αGC vaccine prepared by the same manner as described in Example <1-2> by intravenous injection at different cell concentrations. Serum of the naive mice was used as a control. Ten days later, blood was collected by eye bleeding, which stood at room temperature for 2 hours, followed by centrifugation at 8000 rpm for 10 minutes to separate serum. To examine anti-Her-2/neu antibody production in serum, HER-2/CT26, Her-2/neu expressing murine cancer cell line, was stained with the serum at 4° C. for 60 minutes. Binding capacity of the mouse antibody to HER-2/CT26 cells was investigated using FITC-labeled secondary anti-mouse antibody by flow cytometry.

As a result, the highest antibody production was observed in the group treated with 2×10⁶ cells and significant antibody production was detected in the group treated with 1×10⁶ or 5×10⁵ cells (FIG. 12). However, antibody production was not detected in the group treated with less than 2.5×10⁵ cells.

Example 7

Activation of Antigen Peptide-Specific Cytotoxic T Lymphocytes by IMC Vaccine Loaded with αGalcer and Ovalbumin Peptide To investigate whether the IMC vaccine could activate antigen specific cytotoxic T lymphocytes against another various antigens except Her-2/neu, so as to induce cytotoxic immune responses, in vivo CTL assay was performed using IMC vaccine loaded with αGalCer and OT-1 peptide (H-2K$^b$-presented ovalbumin 257-264 peptide, SEQ. ID. NO: 1, SIINFEKL) of ovalbumin which has been generally used as a model antigen.

Particularly, murine thymoma cell line, EL4 cells (ATCC, USA) were transplanted into C57BL/6 mice (Orient, Korea). About 4 weeks later when the tumor volume reached at least 1500 mm³, splenocytes were isolated from the mice, followed by homogenization. B220+B cells were eliminated by using anti-B220 microbeads (Miltenyibiotec, Germany).

These cells were incubated in a CO₂ incubator for 14 hours together with αGalCer (1.5 μg/ml) or vehicle (0.5% Tween in PBS). CD11b+ cells were obtained therefrom by using anti-CD11b microbeads (Miltenyibiotec, Germany). Then, 2 μg/ml of OT-1 peptide was loaded thereto for one hour. As a result, IMC vaccine was prepared.

Particularly, C57BL/6 mice were immunized with the IMC/pep or IMC/pep/αGalCer prepared by the same manner as described above. Ten days later, in vivo CTL assay was performed. First, naive splenocytes were divided into two groups: one group was loaded with OT-1 peptide (2 μg/ml; Anygen, Korea) and labeled with 20 μM CFSE (carboxyfluorescein diacetate succinimidyl ester, Invitrogen, USA) (CFSE$^{high}$) and the other group was labeled with 2.5 μM CFSE without peptide loading (CFSE$^{low}$, used as a control). Equal amounts of the two group cells were mixed and administered to the immunized mice. On the next day, the CFSE$^{high}$ and CFSE$^{low}$ cell groups in splenocytes were analyzed by flow cytometry.

Figure 13:
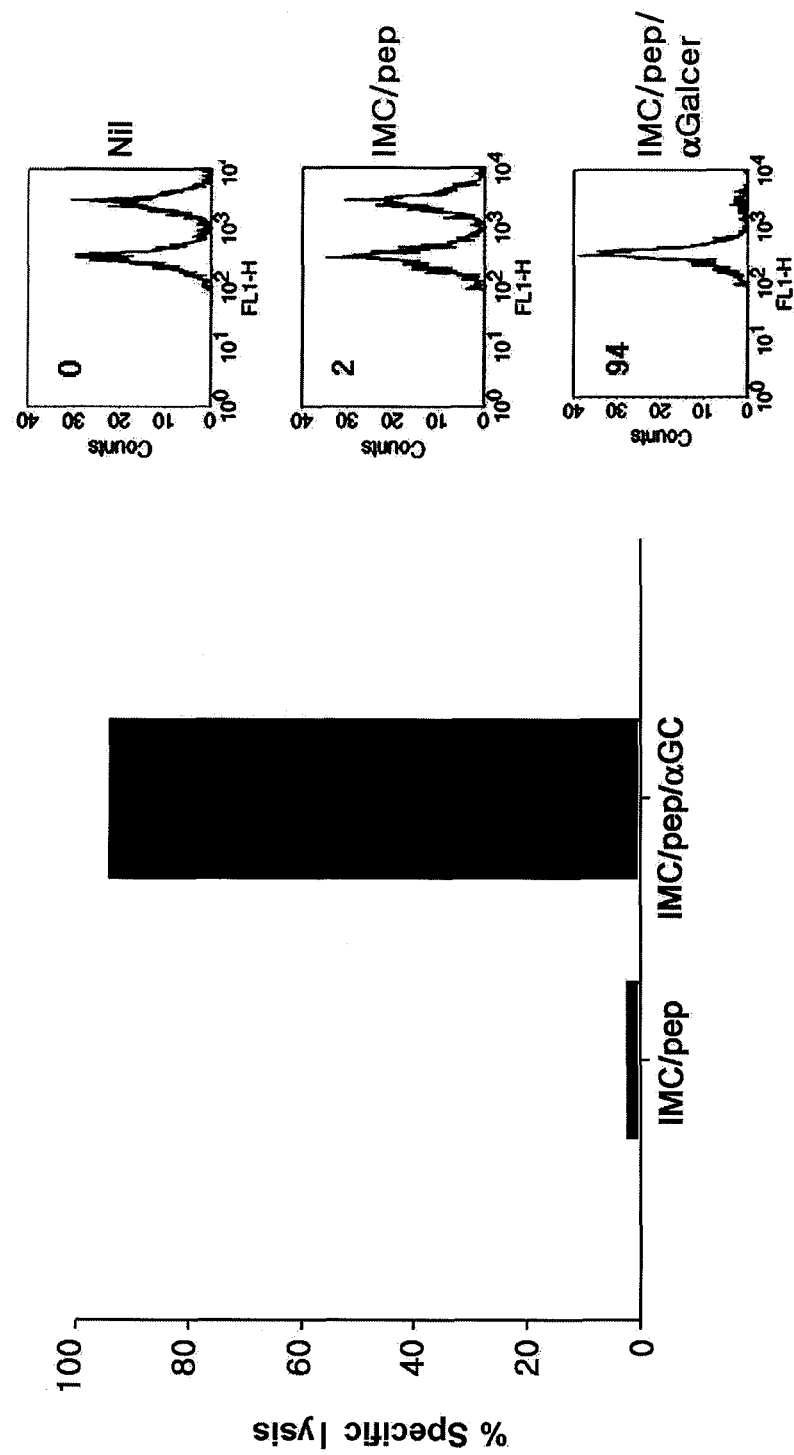
FIG. 13 is a diagram illustrating the activity of antigen peptide-specific cytotoxic T lymphocytes induced by IMC vaccine loaded with αGalCer and OT-1 antigen peptide.

As a result, as shown in FIG. 13, cytotoxic immune response was hardly detected in the group treated with IMC/pep, similarly with the non-treated group. On the contrary, significant cytotoxic immune response approaching 100% was detected in the group immunized with IMC/pep/αGalCer. That is, the administration of IMC/pep/αGalCer induced effective cytotoxic immune response in the foreign antigen, ovalbumin model, compared with the IMC vaccine loaded with an antigen peptide alone (IMC/pep). The above results indicate that the effective immune responses induced by the IMC vaccine are not limited to a specific antigen but applied to various antigens.

Manufacturing Example 1

A Method for Producing Injectable Solution Comprising Monocyte/AdHM/αGC Vaccine as an Active Ingredient Injectable solution of the anticancer vaccine of the present invention was prepared as follows.

α-galactosylceramide (1~2 μg/ml), monocyte/AdHM/αGC vaccine (5×10⁶ cells/ml), peptide (1~2 μg/ml), 5'-chloro-3,2'-dihydroxychalcone or 5'-chloro-2,3'-dihydroxychalconehydrochloride (1 g), sodium chloride (0.6 g) and ascorbic acid (0.1 g) were dissolved in distilled water, resulting in 100 ml of solution. The solution was filled in a bottle, which was sterilized at 120° C. for 30 minutes.

Manufacturing Example 2

A Method for Producing Injectable Solution Comprising IMC/AdHM/αGC Vaccine as an Active Ingredient Injectable solutions of the anticancer vaccine of the present invention were prepared as follows.

α-galactosylceramide (1~2 μg/ml), IMC/AdHM/αGC vaccine (8×10⁶ cells/ml), peptide (1~2 μg/ml), 5'-chloro-3,2'-dihydroxychalcone or 5'-chloro-2,3'-dihydroxychalconehydro chloride (1 g), sodium chloride (0.6 g) and ascorbic acid (0.1 g) were dissolved in distilled water, resulting in 100 ml of solution. The solution was filled in a bottle, which was sterilized at 120° C. for 30 minutes.

SEQUENCE LIST TEXT

SEQ. ID. NO: 1 is the sequence of H-2 Kb-presented ovalbumin 257-264 peptide.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An immunotherapeutic vaccine comprising immature myeloid cells (IMCs) loaded with a natural killer T cell ligand and a target antigen, the IMCs comprising natural killer T cell ligand loaded on CD1d and a target antigen loaded on major histocompatibility complex (MHC) molecules,
   wherein the IMCs are obtained from a tumor-bearing subject;
   wherein the IMCs express GR-1 and CD11b simultaneously on their surface;
   wherein the natural killer T cell ligand is α-galactosylceramide;
   wherein the target antigen is a fragment of a full-length protein derived from a tumor or a pathogen; and
   wherein the vaccine activates cytotoxic T cells specific for said target antigen.

2. The immunotherapeutic vaccine according to claim 1, wherein the pathogenic antigen is a bacterial antigen selected from the group consisting of *Bordetella pertussis* antigen, tetanus toxoid, diphtheria toxoid, *Helicobacter pylori* antigen, pneumococcal antigen, tuberculosis antigen, cholera antigen, staphylococcal antigen, *shigella* antigen, *Borrelia* sp. antigen, *Candida albicans* antigen, and *Plasmodium* antigen.

3. The immunotherapeutic vaccine according to claim 1, wherein the pathogenic antigen is a viral antigen selected from the group consisting of influenza virus antigen, human papilloma virus (HPV) antigen, vesicular stomatitis virus antigen, cytomegalovirus (CMV) antigen, hepatitis virus antigen, respiratory syncytial virus (RSV) antigen, herpes simplex virus (HSV) antigen, human immunodeficiency virus (HIV) antigen, and combinations thereof.

4. The immunotherapeutic vaccine according to claim 1, wherein the tumor antigen is selected from the group consisting of Her-2/neu, Proteinase 3, Wilm's Tumor associated gene (WT-1), murinoglobulin, prostatic acid phosphatase (PAP), prostate-specific antigen (PSA), prostate-specific membrane antigen (PSMA), G250, melanoma antigen (MAGE), B melanoma antigen (BAGE), G melanoma antigen (GAGE), NY-ESO-1 (New York-Esophageal cancer-1), tyrosinase, tyrosinase-related protein-1 (TRP-1), tyrosinase-related protein-2 (TRP-2), gp100 (glycoprotein 100), Melanoma antigen recognized by T cell-1 (MART-1), melanocortin-1 receptor (MC1R), cyclin D-dependent kinase, caspase-8, β-catenin, BCR/ABL, human papillomavirus (HPV) E6/E7, Epstein-Barr virus (EBV) latent membrane protein 2A (LMP2a), Hepatitis C virus (HCV), Human herpes virus, 5T4, carcinoembryonic antigen (CEA), p53, and α-fetoprotein.

5. The immunotherapeutic vaccine according to claim 1, wherein the target antigen is in the form of a glycoprotein.

6. A method for treating a cancer or an infectious disease comprising administering to a subject an immunotherapeutic vaccine of claim 1.

7. A composition comprising isolated immature myeloid cells (IMCs) loaded with a natural killer T cell ligand and a target antigen, the IMCs comprising a natural killer T cell ligand loaded on CD1d and a target antigen loaded on major histocompatibility complex (MHC) molecules,
   wherein the IMCs are obtained from a tumor-bearing subject;
   wherein the IMCs express Gr-1 and CD11b simultaneously on their surface;
   wherein the natural killer T cell ligand is α-galactosylceramide;
   wherein the target antigen is a fragment of a full-length protein derived from a tumor or a pathogen; and
   wherein the composition activates cytotoxic T cells specific for said target antigen.

* * * * *